| United States Patent [19] | [11] | 4,337,250 |
|---|---|---|
| Welch et al. | [45] | Jun. 29, 1982 |

[54] HEXAHYDRO-TRANS- AND TETRAHYDROPYRIDOINDOLE NEUROLEPTIC AGENTS

[75] Inventors: Willard M. Welch, Mystic; Charles A. Harbert, Waterford, both of Conn.

[73] Assignee: Pfizer Inc., New York, N.Y.

[21] Appl. No.: 225,569

[22] Filed: Jan. 16, 1981

Related U.S. Application Data

[60] Continuation-in-part of Ser. No. 182,177, Aug. 28, 1980, abandoned, which is a division of Ser. No. 61,573, Jul. 30, 1979, Pat. No. 4,252,811.

[51] Int. Cl.³ .................. C07D 471/14; C07D 413/06; A61K 31/44; A61K 31/535
[52] U.S. Cl. ............................... 424/248.57; 546/87; 544/54; 544/126; 544/238; 544/316; 544/361; 424/248.51; 424/250; 424/251; 424/256
[58] Field of Search .......................... 546/87, 84, 85; 544/126, 54, 316, 238, 361; 424/256, 250, 251, 248.57, 248.51

[56] References Cited

U.S. PATENT DOCUMENTS

| 3,687,961 | 8/1972 | Bernstein et al. | 546/87 |
|---|---|---|---|
| 3,983,239 | 9/1976 | Nagai et al. | 424/256 |
| 3,991,199 | 11/1976 | Berger | 424/256 |
| 4,001,263 | 1/1977 | Plattner et al. | 546/85 |
| 4,141,980 | 2/1979 | Berger | 424/256 |
| 4,224,329 | 9/1980 | Welch et al. | 424/256 |
| 4,252,811 | 2/1981 | Welch et al. | 424/256 |

*Primary Examiner*—Alan L. Rotman
*Attorney, Agent, or Firm*—Charles J. Knuth; Albert E. Frost; Robert K. Blackwood

[57] ABSTRACT

Derivatives of 2,3,4,5-tetrahydro-1H-pyrido[4,3-b]-indole and of (+)enantiomeric, mixtures of (+) and (−)enantiomeric or (±)racemic 2,3,4,4a,5,9b-hexahydro-4a,9b-trans-1H-pyrido[4,3-b]indole, substituted at the 5-position with an aryl group and at the 2-position with a carbonylaminoalkyl group or an aminoalkyl group, are neuroleptic agents useful in the treatment of certain psychoses and neuroses.

12 Claims, No Drawings

HEXAHYDRO-TRANS- AND TETRAHYDROPYRIDOINDOLE NEUROLEPTIC AGENTS

CROSS REFERENCE TO RELATED APPLICATIONS

This application is a continuation-in-part of pending application Ser. No. 182,177 filed Aug. 28, 1980 now abandoned, which is a division of pending application Ser. No. 061,573 filed July 30, 1979 now Pat. No. 4,252,811.

BACKGROUND OF THE INVENTION

The successful treatment of schizophrenic behavior using antipsychotic tranquilizers such as chlorpromazine has stimulated research to find other neuroleptic agents having improved biological profiles. One such class of compounds is the 2,3,4,4a,5,9a-hexahydro-1H-pyrido[4,3-b]-indoles and the 2,3,4,5-tetrahydro-1H-pyrido[4,3-b]indoles. The basic ring structures are

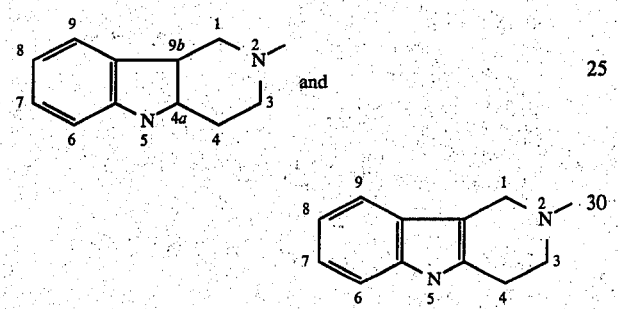

and

The stereochemistry at positions 4a and 9b in the hexahydro series can be cis or trans, each of which can exist in racemic($\pm$) or enantiomeric($+$ or $-$) forms. Examples of hexahydro- and tetrahydro-pyridoindoles that are useful as tranquilizers, neuroleptic agents, analgesics, sedatives, muscle relaxants and hypotensive agents are given in the following U.S. Pat. Nos.: 3,687,961; 3,983,239; 3,991,199; 4,001,263; 4,141,980; and 4,224,329.

Potent neuroleptic activity has now been discovered for novel 2,3,4,4a,5,9b-hexahydro-4a,9b-trans-1H-pyrido[4,3-b]indoles and 2,3,4,5-tetrahydro-1H-pyrido[4,3-b]indoles substituted at the 5-position with an aryl group and the 2-position with an aminoalkyl group or a carbonylaminoalkyl group (the carbonyl group either further substituted with a radical such as hydrogen, alkyl, aryl, aralkyl or alkoxy; or bridged to the amine by a diradical such as alkano[—(CH$_2$)$_i$—, wherein i is 3 to 5] or a 3–6 atom chain containing various combinations of carbonyl, alkano, alkeno-(CH=CH—), o-benzeno

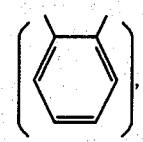

imino, sulfur or oxygen.

SUMMARY OF THE INVENTION

The neuroleptic agents of the present invention are ($+$)enantiomeric, a mixture of ($+$) and ($-$)enantiomeric or ($\pm$)racemic 2,3,4,4a,5,9b-hexahydro-4a,9b-trans-1H-pyrido[4,3-b]indole derivatives of formulae:

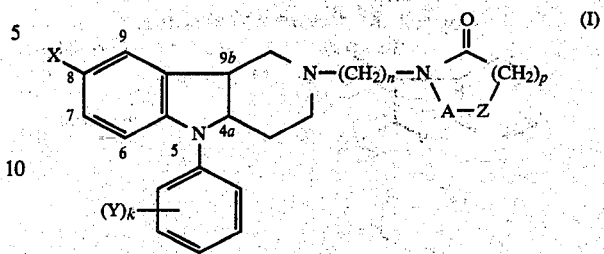

wherein
k is an integer of value 1 or 2;
n is an integer of value 2 to 9;
p is 0 or 1;
X and Y are each independently H, F, Cl, Br, OCH$_3$, CH$_3$ or CH$_2$CH$_3$;
A is methano(—CH$_2$—), ethano(—CH$_2$CH$_2$—), propano (—CH$_2$CH$_2$CH$_2$—), etheno(—CH=CH—), o-benzeno

or a mono or disubstituted form of o-benzeno, the monosubstituent and each of the disubstituents being independently F, Cl, Br, OCH$_3$, CH$_3$ or CH$_2$CH$_3$;
with the proviso that when A is methano, p is 1, thus excluding 4-membered rings which are not within the scope of the present invention;
Z is methano, oxygen, sulfur or NR$^2$; and
R$^2$ is H, (C$_1$–C$_5$)alkyl, phenyl, benzyl or a ring mono- or disubstituted form of phenyl or benzyl, the monosubstituent and each of the disubstituents being independently F, Cl, Br, OCH$_3$, CH$_3$ or CH$_2$CH$_3$;

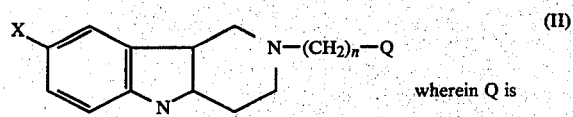

wherein Q is

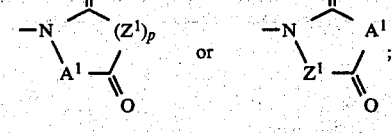

Z$^1$ is methano or NR$^2$;
k, n, X, Y, p and R$^2$ are as defined above;
A$^1$ is oxygen, NR$^3$, methano, ethano, etheno, o-benzeno, or a mono- or disubstituted form of o-benzeno, the mono and each of the disubstituents being independently F, Cl, Br, OCH$_3$, CH$_3$ or CH$_2$CH$_3$; and
R$^3$ is independently a value of R$^2$ as defined above;

with the proviso that when $A^1$ is methano, oxygen or $NR^3$, p is 1, again to exclude 4-member rings as outside the scope of the present invention;

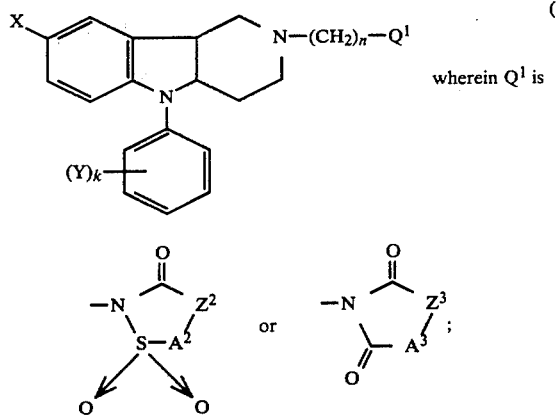

(III)

wherein $Q^1$ is

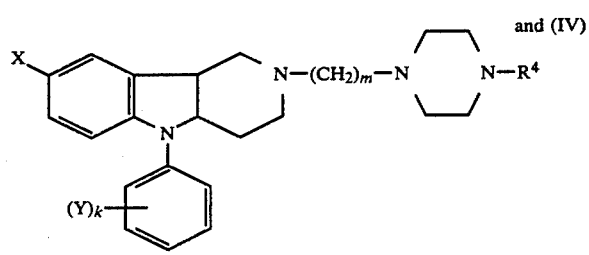

$A^2$ and $Z^2$ when taken together and $A^3$ and $Z^3$ when taken together are ethano, propano, etheno, o-benzeno or a mono- or disubstituted form of o-benzeno, the mono and each of the disubstituents being independently F, Cl, Br, $OCH_3$, $CH_3$ or $CH_2CH_3$;

$A^3$ when taken separately is methano, ethano, etheno, o-benzeno or a mono- or disubstituted form of o-benzeno, the monosubstituents and each of the disubstituents being independently F, Cl, Br, $OCH_3$, $CH_3$ or $CH_2CH_3$;

$Z^3$ when taken separately is oxygen, sulfur or $NR^2$; and k, n, X, Y and $R^2$ are as defined above;

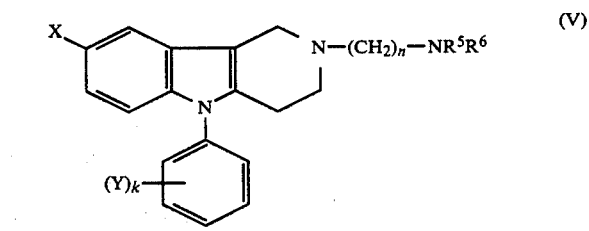 and (IV)

wherein
k, X and Y are as defined above;
m is an integer of value 1 to 6; and
$R^4$ is H, $(C_1-C_5)$alkyl, phenyl, benzyl, $(C_1-C_8)$alkanoyl, $(C_1-C_8)$alkoxycarbonyl, benzoyl, phenylacetyl, $(C_1-C_8)$alkylsulfonyl, phenylsulfonyl, or a ring mono- or disubstituted form of phenyl, benzyl, benzoyl, phenylacetyl or phenylsulfonyl, the monosubstituent and each of the disubstituents being independently F, Cl, Br, $OCH_3$, $CH_3$ or $CH_2CH_3$; and 2,3,4,5-tetrahydro-1H-pyrido[4,3-b]indoles of the formula

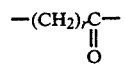 (V)

wherein k, n, X and Y are as defined above;
$R^5$ taken separately is hydrogen;
$R^6$ taken separately is $(C_1-C_8)$alkanoyl or $(C_1-C_8)$alkoxycarbonyl; and
$R^5$ and $R^6$ taken together are $$-(CH_2)_r C- \\ \parallel \\ O$$

wherein r is an integer of value 3 to 5.

Also encompassed by the present invention are the pharmaceutically acceptable salts of the compounds defined above, pharmaceutical compositions of these compounds and a method of treating psychoses and neuroses in patients requiring major tranquilization which comprises administering to the patient by the oral or parenteral (intravenous, intramuscular or subcutaneous) route an effective amount of one of these compounds, alone or as a component of a pharmaceutical composition.

In all cases, the preferred compounds have the values: X is F, k is 1; Y is F (substituted at the para position) and n is 3 to 6 or m is 2 to 4. In the cases of 2,3,4,4a,5,9b-hexahydro-4a,9b-trans-1H-pyrido[4,3-b]indoles of the formulae (I) through (IV), the preferred compounds are the derivatives of either the racemic or more particularly of the (+)enantiomeric form.

Furthermore, the most preferred compounds of the formula (I) are those wherein A is ethano; within the subgroup preferred compounds have p as 1 and Z as methylene, or p as 0 and Z as oxygen. The preferred compounds of the formula (II) have p as 1 with $A^1$ as methano and $Z^1$ as $NR^2$ (the preferred values of $R^2$ in this subgroup are H and benzyl) or p as 0 with $A^1$ as o-benzeno. The preferred compounds of the formula (III) have as the terminal group of the sidechain

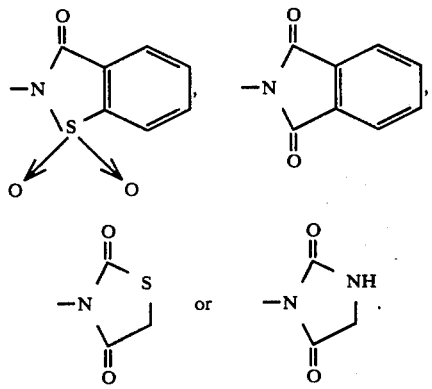

The most preferred compounds of the structure (IV) have $R^4$ as alkanoyl, alkoxycarbonyl, benzoyl or phenylacetyl; most highly preferred in this series are those compounds wherein $R^4$ is acetyl. The most preferred compounds of the structure (V) have $R^5$ as hydrogen and $R^6$ as acetyl or carbethoxy, or $R^5$ and $R^6$ taken together as $$-(CH_2)_3-C- \\ \parallel \\ O$$

Exemplary of the side chain terminal groups of the formula (I) are:

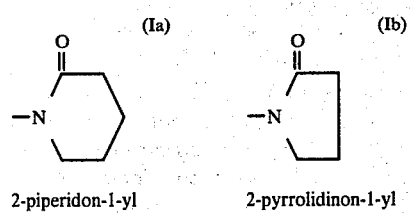

2-piperidon-1-yl (Ia)  2-pyrrolidinon-1-yl (Ib)

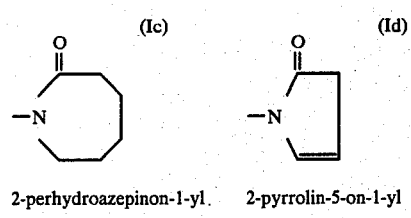

2-perhydroazepinon-1-yl (Ic)  2-pyrrolin-5-on-1-yl (Id)

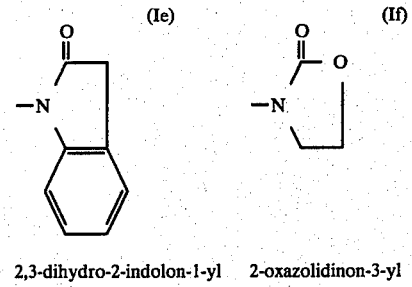

2,3-dihydro-2-indolon-1-yl (Ie)  2-oxazolidinon-3-yl (If)

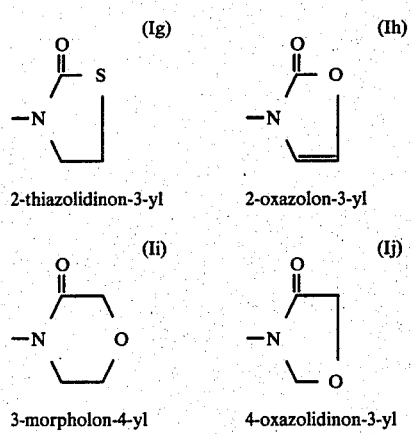

2-thiazolidinon-3-yl (Ig)  2-oxazolon-3-yl (Ih)

3-morpholon-4-yl (Ii)  4-oxazolidinon-3-yl (Ij)

2(1H)-oxazolon-3-yl (Ik)  2,3-dihydro-2-benz[d]oxazolon-3-yl (Il)

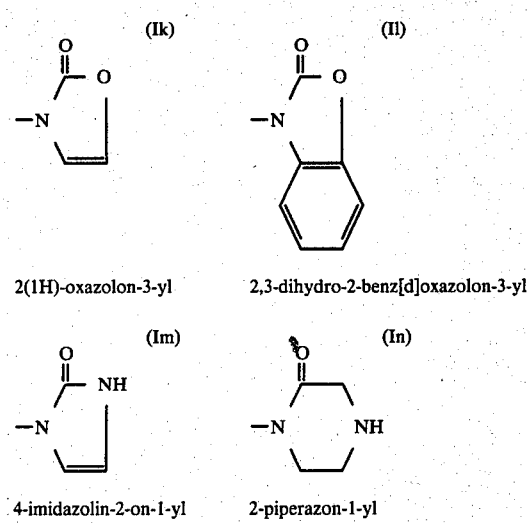

4-imidazolin-2-on-1-yl (Im)  2-piperazon-1-yl (In)

Exemplary of the sidechain terminal groups of the formula (II) are:

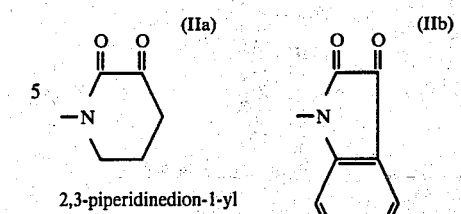

2,3-piperidinedion-1-yl (IIa)  2,3-indolinedion-1-yl (IIb)

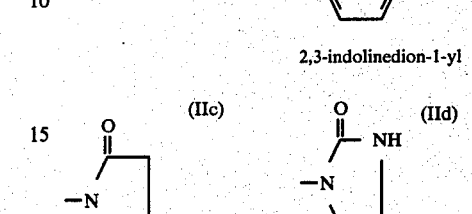

3,5-isoxazolidinedione-2-yl (IIc)  1,2,4-oxadiazolidine-3,5-dion-2-yl (IId)

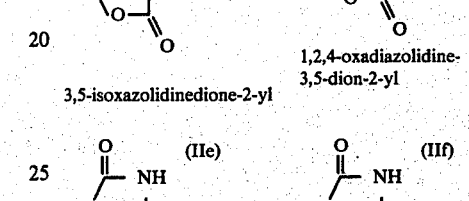

1,2,4-triazolidine-3,5-dion-2-yl (IIe)  2,4-imidazolidinedione-1-yl (IIf)

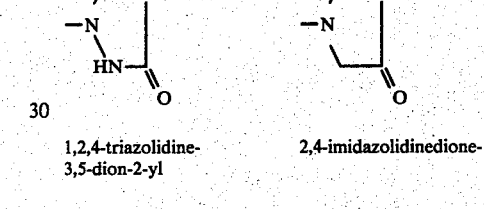

1,2,3-tetrahydro-3,6-pyridazinedion-1-yl (IIg)  3,5-pyrazolidinedion-1-yl

Exemplary of the sidechain terminal groups of the formula III are:

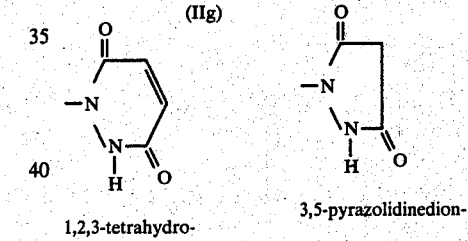

1,1-dioxo-3(2H)-benz-[d]isothiazolon-2-yl (IIIa)  2,3-dihydro-2,3(1H)-isoindoledion-2-yl (IIIb)

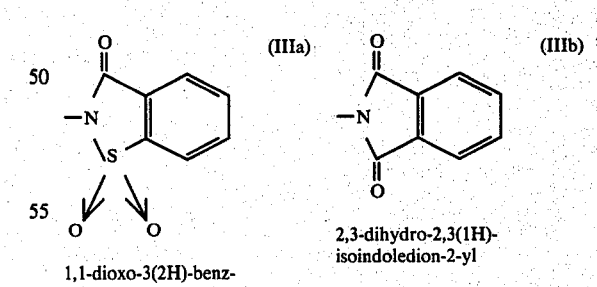

2,4-thiazolidinedion-3-yl (IIIc)  3,4,5,6-tetrahydro-1,3(2H)-thiazine-2,4-dion-3-yl (IIId)

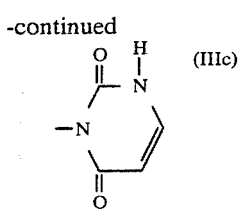

2,4-imidazolidindion-3-yl    2,4(1H,3H)-pyrimidindion-3-yl

DETAILED DESCRIPTION OF THE INVENTION

The compounds of the present invention are readily prepared by methods which are detailed in the following paragraphs. For purposes of discussion, the instant 2,3,4,4a,5,9b-hexahydro-4a,9b-trans-1H-pyrido[4,3-b]indole and 2,3,4,5-tetrahydro-1H-pyrido[4,3-b]indole nuclei,

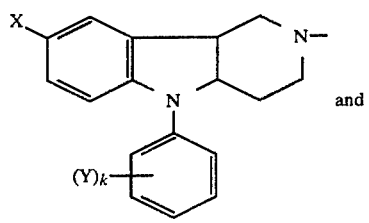

and

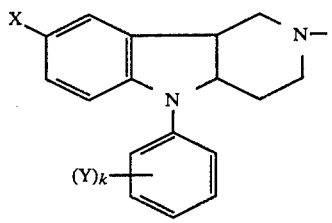

wherein k, X and Y are as defined above, will be referred to, respectfully, as R and R'', or generically as R'.

Compounds of the present invention can be regarded as synthesizable from three synthons, viz., (a) (±)RH, (+)RH or R''H;
(b) an alpha,omega-disubstituted straight chain alkane (or alkane precursor); and
(c) a side chain terminal group, or terminal group precursor.

Synthesis of 2-piperidon-1-yl derivatives [formula I, p=1, Z=methano, A=ethano; formula V, R⁵ and R⁶ are taken together as (CH₂)₃CO] illustrate the basic methods of approach which are applied.

Method A: (a) + (b) (c) ⟶ (a) (b) (c)

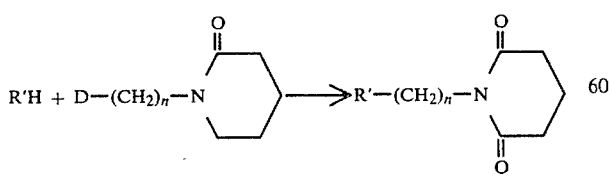

wherein n and R' are as defined above and D represents a displaceable group (Cl, Br, I, CH₃SO₂O, etc.). This nucleophilic displacement reaction is carried out in a reaction inert solvent, such as a lower aliphatic ketone (e.g., acetone, 2-butanone, 3-methyl-2-butanone, 3-methyl-2-pentanone), a lower alkanol (e.g., ethanol, 2-propanol), or a lower aliphatic amide (e.g., dimethylformamide, dimethyl acetamide). The pyridoindole (RH, R''H) is preferably maintained in the form of the much more reactive free base by the addition of at least one equivalent of a base such as sodium carbonate to the reaction mixture. When D is other than I, iodide ion can be added to enhance the reaction rate, if desired. Temperature is not critical, the temperature usually being elevated (e.g., 50°–150° C.) to enhance the rate of reaction, but not so high as to cause undesirable levels of thermal degradation of the products and/or reactants.

The pyrido[4,3-b]indoles required for these syntheses and the further syntheses detailed below are available by the methods of U.S. Pat. Nos. 3,687,961; 3,983,239; 3,991,199; 4,001,263; 4,141,980 and 4,224,329.

The piperidone derivatives are readily available by reaction of the anion of 2-piperidone with a di-substituted alkane, D(CH₂)ₙD, wherein D and n are as defined above and the D groups can be the same or different. Bis-displacement is minimized by using excess D(CH₂)ₙD and/or by one group being more readily displaceable [e.g., Cl(CH₂)ₙBr].

Reaction conditions (solvent and temperature) are generally as described above, except that protic solvents (e.g., alcohols), which are more acidic than 2-piperidone, are avoided.

The same approach is broadly available for the synthesis of many other compounds of the present invention. For example, those compounds wherein the sidechain terminus is alkanoylamino, alkoxycarbonylamino, (Ib) to (Ij), (IIa) to (IIc), (IIIa) to (IIIf), or N-substituted variants thereof. In other cases, for example, those compounds wherein the sidechain terminus is piperazino or of the formula (IId)–(IIh), the same approach is just as applicable when equally reactive or more reactive nitrogen atoms are already substituted, e.g.,

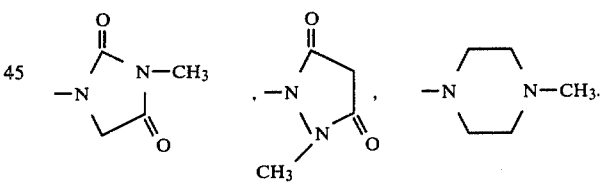

If the substituent is a group such as benzyl, the substituent can be removed by hydrogenolysis affording a synthesis of those compounds wherein the terminus is unsubstituted piperazino, or (IId) to (IIh), e.g.,

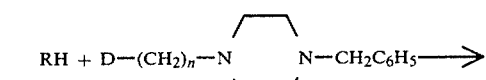

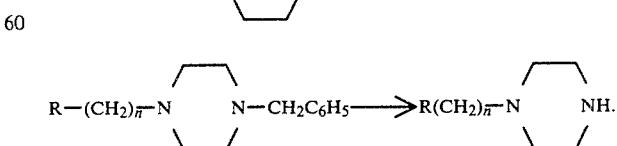

Method B: (a) (b) + (c) ⟶ (a) (b) (c)

-continued

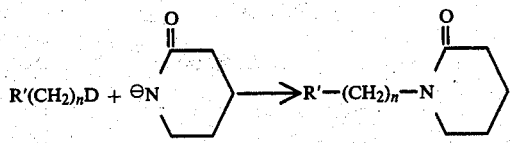

wherein R', n and D are as defined above. This nucleophilic displacement is carried out using substantically equivalent quantities of the reactants, otherwise under conditions as described above for the synthesis of

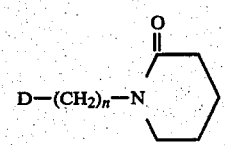

While the substituted pyrido[4,3-b]indoles are potentially available by a number of routes, the preferred route is:

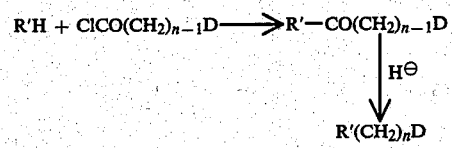

The piperidone anion is generally formed in situ by reaction of the piperidone with sodium hydride.

This approach is also broadly applicable to the synthesis of other compounds of this invention, applying the principles enunciated in the preceding section, e.g.,

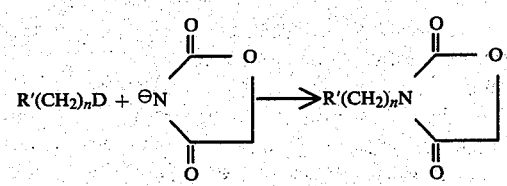

Method C: (a) (b') (c) ⟶ (a) (b) (c)

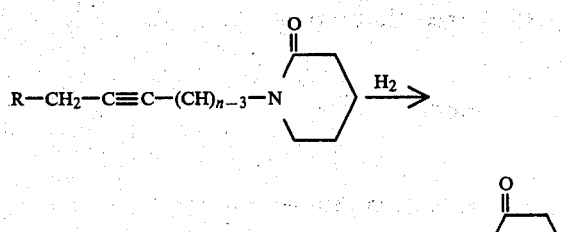

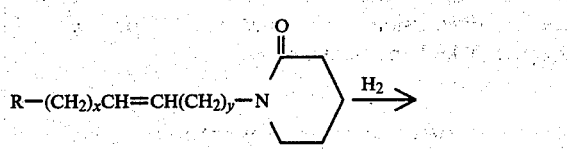

-continued

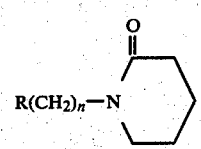

wherein R and n are as defined above, and x and y are each 1 or greater and $x+y-2=n$. These are hydrogenation reactions, carried out in an inert solvent under a hydrogen atmosphere in the presence of a hydrogenation catalyst, preferably a noble metal catalyst including platinum, palladium, rhodium and ruthenium, either of the supported or non-supported type, as well as the known catalytic compounds thereof such as the oxides, chlorides, etc. Specific examples of suitable catalysts are 5% palladium on carbon, 5% palladium on barium carbonate, 5% rhodium on carbon, rhodium chloride, platinum oxide and 5% ruthenium on carbon. The temperature and pressure of the hydrogenation are not critical, being generally carried out in a temperature range of 10°–90° C., conveniently 20°–50° C., at a pressure ranging from subatmospheric to 100 atmospheres, or more. A convenient operating pressure is 2–3 atmospheres.

The starting materials required for these syntheses are generally available by following method A above, but substituting an unsaturated compound for $D(CH_2)_nD$, e.g.,

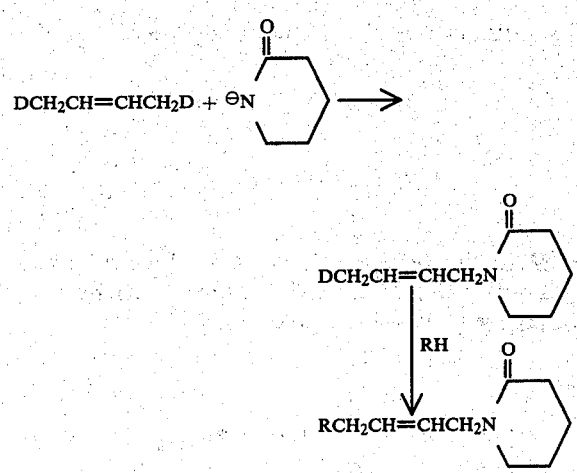

Alternatively, the following synthetic route is available:

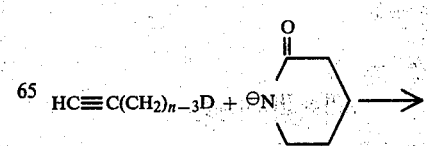

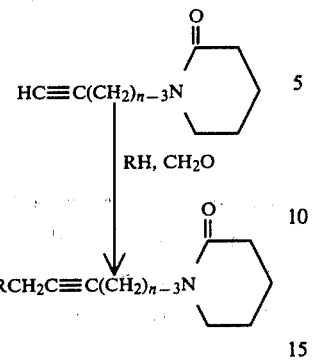

The first stage nucleophilic displacement reaction is carried out under conditions described above. The second stage formaldehyde bridging of the acetylene to RH, is carried out in a reaction inert solvent (a lower alkanol is well-suited) employing the free base form of RH, an equivalent of formaldehyde (conveniently as a 30% aqueous solution) and an equivalent of the acetylene in the presence of cuprous chloride as catalyst. Temperature is not critical (e.g., 0°–50° C.), the reaction being conveniently carried out at ambient temperature (20°–25° C.).

This approach is further available for the synthesis of many other compounds of the present invention, when the terminus is free of groups which are subject to significant hydrogenation side-reaction under the conditions employed for hydrogenation of the unsaturation. In the case of benzyl protecting groups, these can generally be removed in the same reaction as reduction of an unsaturated group, e.g.,

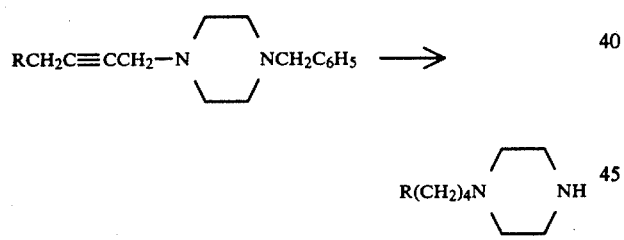

When the terminus is free of carbonyl, hydride reduction of amide precursors is a further viable route to compounds of the present invention, e.g.,

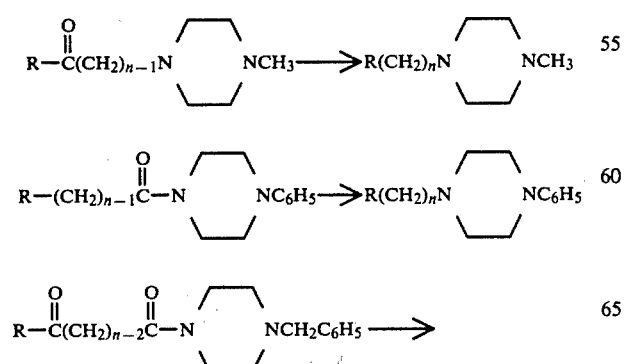

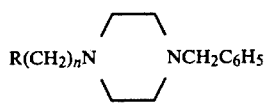

A further variation is to alternatively or simultaneously reduce a different terminal amide group, e.g.,

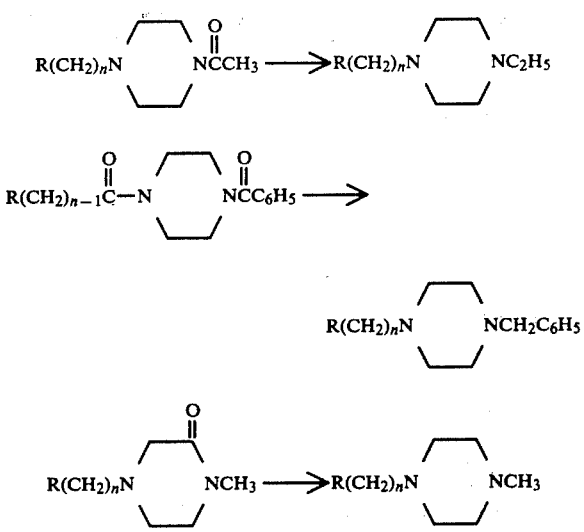

These hydride reductions are conveniently carried out with excess lithium aluminum hydride (two equivalents are required for each amide function) in an ether solvent (e.g., diethyl ether, tetrahydrofuran, dioxane) in the temperature range 0°–50° C. Alternatively, such amides are reduced with diborane or aluminum hydride in the same type of solvent, or reacted with triethyloxonium fluoroborate (e.g., in methylene chloride at 20°–30° C.) and then reduced with sodium borohydride in a lower alkanol (e.g., ethanol) at 0°–25° C.

It will be noted that the approach of Method C, as detailed above, has particular value in the synthesis of the hexahydropyrido[4,3-b]indoles, specified as RH, since the tetrahydro compounds (R″H) have a double bond which can complicate hydrogenation of an olefin. However, when the terminus of a tetrahydro compound is a precursor amine, then the above lithium aluminum hydride reduction of amide or nitrile is well suited, e.g.,

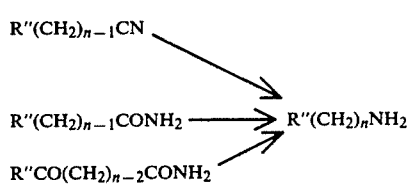

Diborane is, of course, not employed unless simultaneous conversion of tetrahydro to hexahydropyrido[4,3-b]indole is desired.

Method D: (a) (b) (c′) ⟶ (a) (b) (c)

-continued

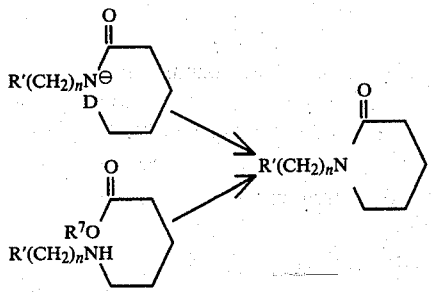

wherein n, R' and D are as defined above and $R^7$ is $(C_1-C_5)$alkyl. The nucleophilic displacement of D is carried out under conditions detailed above. The anion can be preformed or formed in situ with a strong base such as sodium hydride. The intermediate is conveniently derived by acylation of amine:

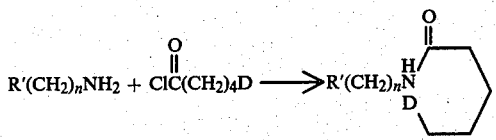

The intermediate amide need not be isolated, but can be formed in situ and then converted to the anion. The acylation is carried out under mild conditions (e.g., −25° to 35° C.), usually in a reaction inert solvent in the presence of at least one equivalent of inorganic base or of tert-amine (e.g., triethylamine, N-methylmorpholine).

The alternative process, cyclization of the amino ester precursor, is accomplished by mere heating of the free base form of the amino ester in a reaction inert solvent, conveniently an aromatic hydrocarbon such as benzene, toluene or xylene. Temperature is not critical (e.g., 80°–150° C., preferably 100°–125° C.) so that the reaction proceeds at a reasonable rate, but thermal degradation is minimized. The preferred value of $R^7$ is methyl, since cyclization occurs most rapidly at the lowest possible temperatures. The amino esters are conveniently prepared by alkylation of amine:

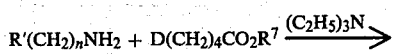

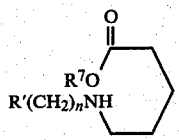

or reductive amination of aldehyde:

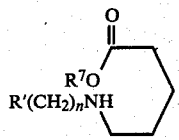

In modified form, the reactions described immediately above can be applied to the preparation of other compounds of the present invention, e.g.,

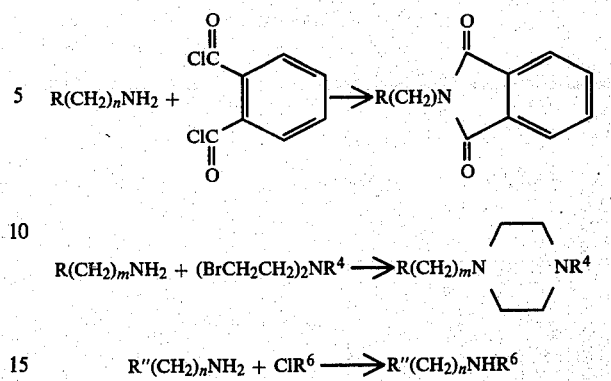

wherein n, m, R, R'', $R^4$ and $R^6$ are as defined above.

In further modified form the basic approach of Method D is broadly applicable to the synthesis of the compounds of the present invention, that is, to build up the side chain terminus from suitable precursor, e.g.,

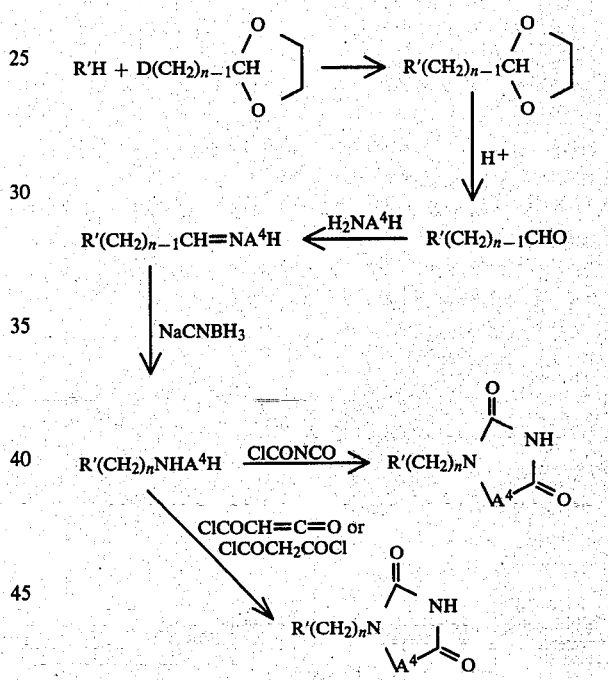

wherein $A^4$ is oxygen or $NR^3$ and n, R' and $R^3$ are as defined above.

The pharmaceutically acceptable salts of the derivatives can be prepared by reaction with either about 1 molar equivalent or about 2 molar equivalents of an organic or mineral acid in either aqueous or nonaqueous solution. Since the compounds of the present invention are generally dibasic, either mono salts or bis salts are thereby formed, depending upon the molar equivalent of acid. Those compounds which are tribasic can, of course, form a tris salt, in which case three molar equivalents of acid can be used. Suitable salt forming acids include hydrochloric, hydrobromic, hydroiodic, sulfuric, phosphoric, methanesulfonic, p-toluenesulfonic, lactic, citric, tartaric, succinic, maleic and gluconic acids. The salt can be isolated by removal of the solvent in vacuo or in an appropriate case, by precipitation.

The derivatives are useful as neuroleptic agents in the treatment of mental disorders and illnesses including schizophrenia, psychoses and neuroses. Symptoms requiring such treatment include anxiety, aggression, agitation, depression, hallucinations, tension and emotional or social withdrawal. In general, the derivatives exhibit major tranquilizing activity but have fewer side effects than the drugs presently in use.

The derivatives can be formulated in a variety of pharmaceutical preparations which contain the derivative alone or in combination with pharmaceutical carriers such as inert solid diluents, aqueous solutions or various non-toxic, organic solvents and in dosage forms such as gelatin capsules, tablets, powders, lozenges, syrups, injectable solutions and the like. Such carriers include water, ethanol, gelatins, lactose, starches, vegetable oils, petroleum jelly, gums, glycols, talc, benzoyl alcohols, and other known carriers for medicaments. If desired, these pharmaceutical preparations can contain additional material such as preserving agents, wetting agents, stabilizing agents, lubricating agents, absorption agents, buffering agents and isotonic agents.

The derivatives are administered to a patient in need of treatment by a variety of conventional routes of administration such as oral, intravenous, intramuscular or subcutaneous. In general, small doses will be administered initially with a gradual increase in the dose until the optimum level is determined. However, as with any drug the particular dose, formulation and route of administration will vary with the age, weight and response of the particular patient and will depend upon the judgment of his attending physician.

In the usual course of treatment a dose of a derivative of approximately 0.1 mg per day to 100 mg per day will provide effective treatment for the human patient. When the derivative has a prolonged effect, the dose can be administered less frequently, such as every other day or in 1 or 2 divided doses per week.

The tranquilizing activity of the derivatives may be determined using the well known standard procedure-antagonism of amphetamine-induced symptoms in rats. This method has excellent correlation with human efficacy and is taught by A. Weissman, et al., J. Pharmacol. Exp. Ther. 151, p. 339 (1966) and by Quinton, et al., Nature 200, p. 178, (1963), and more particularly by Harbert et al., Molecular Pharmacology 17, pp. 38–41 (1980). In detail neuroleptic effects in vivo were estimated by the blockade of amphetamine stereotypy. Rats were placed individually in covered plastic compartments; after a brief period of acclimation in the cages the rats in groups of five were treated intraperitoneally with the test compound at doses separated by 0.5 log units (i.e., . . . 1, 3.2, 10, 32, . . . mg/kg). They were subsequently treated 1, 5, and 24 hr later with d-amphetamine sulfate, 5 mg/kg ip. One hour after each amphetamine challenge, each rat was assessed for its most characteristic cage movement behavior on a 6-point scale [Weissman et al., J. Pharmacol. Exp. Ther. 151, pp. 339–352 (1966)]. These ratings represent increasing degrees of drug effect [Quinton and Haliwell, Nature (London) 200, pp. 178–179 (1963)] and the time of rating chosen coincides with the peak effect of amphetamine [Weissman, Psychopharmacologia 12, pp. 142–157 (1968)]. Scores were dichotomized (cf. Weissman et al., loc. cit.), and approximate $ED_{50}$'s were determined, based on the quantal data. Doses are expressed in terms of the hydrochloride salts. As illustrated by the results tabulated in Table I, this method shows that the compounds of the present invention have excellent tranquilizing activity compared to the standard test drug, chlorpromazine.

So called "intrinsic" tranquilizing neuroleptic activity of the derivatives was determined using $^3H$-spiroperidol binding to dopamine receptor according to the method of Leysen et al., Biochem. Pharmacol. 27, p. 307 (1978) and was adapted from that of Burt et al., Mol. Pharmacol. 12, pp. 800–812 (1976).

Rats (Sprague-Dawley CD males, 250–300 g, Charles River Laboratories, Wilmington, Mass.) were decapitated, and brains were immediately dissected to recover the corpus striatum. The latter was homogenized in 40 vol of ice-cold 50 mM Tris (tris[hydroxymethyl]-aminomethane).HCl buffer, pH 7.7 with a Brinkmann Polytron PT-10. The homogenate was centrifuged twice at 50,000 g for 10 minutes at 0°–4° with rehomogenization of the intermediate pellet in fresh Tris buffer (same volume) in the Polytron. The final pellet was gently resuspended in 90 volumes of cold 50 mM Tris.HCl buffer, pH 7.6, containing 120 mM NaCl, 5 mM KCl, 2 mM $CaCl_2$, 1 mM $MgCl_2$, 0.1% ascorbic acid, and 10 μM pargyline. The tissue suspension was placed in a 37° water bath for 5 minutes and kept ice cold until use. The incubation mixture consisted of 0.02 ml inhibitor solution or vehicle, 1.0 ml tissue preparation, and 0.10 ml $^3H$-spiroperidol (New England Nuclear, 23.6 Ci/mmol) prepared so as to obtain 0.5 nM final concentration. Tubes were incubated in sequence for 10 minutes at 37° in groups of three, after which 0.9 ml from each incubation tube was filtered through Whatman GF/B filters with vacuum. After washing twice with 5 ml of cold tris HCl buffer, pH 7.7, each filter was placed in a scintillation vial with 10 ml Aquasol-2 (New England Nuclear), and each vial was vortexed. Samples were kept at room temperature overnight before determination of radioactivity in a liquid scintillation counter. Binding was calculated as fmoles of $^3H$-spiroperidol bound per milligram of protein. Controls (vehicle or $10^{-7}$ M l-butaclamol), blank ($10^{-7}$ M d-butaclamol) and inhibitor solutions (four concentrations) were run in triplicate. The concentration that reduced binding by 50% ($IC_{50}$) was estimated on semi-log paper. The $IC_{50}$ values in Table I represent means of two or three runs. Insoluble drugs were dissolved in ethanol (1–2% ethanol in final incubation mixture). As illustrated in Table I, this intrinsic method shows that the compounds of the present invention have excellent neuroleptic activity.

The present invention is illustrated by the following examples. However, it should be understood that the invention is not limited to the specific details of these examples.

TABLE I
NEUROLEPTIC ACTIVITY OF 1H-PYRIDO[4,3-b]INDOLES
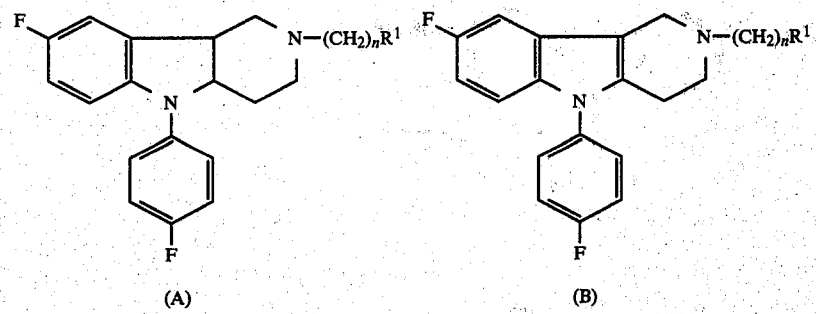
(A)    (B)
| A/B | R[1] | n | Amphetamine Activity[b] (approx. ED$_{50}$ mg/kg i.p.) 1 hr. | 5 hr. | 24 hr. | Inhibition H$^3$-Spiroperidol Binding[c] IC$_{50}$ (nM) |
|---|---|---|---|---|---|---|
| (A) | (piperidinone) | 4 | 0.018 | 0.01–0.032 | 0.056 | 6.2 |
|  |  | 4(+) | 0.04 | 0.01 | 0.11 | 6.8 |
|  |  | 6 | 0.32–1 | <0.32 | 0.32–1 | 9.5 |
| (A) | (oxazolidinone) | 4 | 0.057 | 0.008 | 0.057 | 10 |
|  |  | 6 | <0.1 | <0.1 | 0.1–0.32 | 6.5 |
| (A) | (benzoxazolone) | 4 | >1 | 0.32–1.0 | ~0.32 | 28 |
| (A) | (isatin) | 4 | >1 | 0.32–1.0 | ~3.2 | 42 |
| (A) | (thiazolidinedione) | 4 | 0.18 | 0.11 | 0.36 | 12 |
| (A) | (N-CH$_2$C$_6$H$_5$ hydantoin) | 4 | 1–3.2 | <3.2 | 3.2–10 | 29 |
| (A) | (phthalimide/isoquinolinedione) | 4 | 3.6 | 1.1 | 0.57 | 27 |
| (A) | (hydantoin NH) | 2 | 0.57 | 0.57 | >32 | 26 |
|  |  | 3 | 0.11 | 0.05 | >0.32 | 14 |
|  |  | 6 | 0.18 | 0.033 | >0.32 | 9.4 |
| (A) | (saccharin) | 4 | — | 5.7 | — | 29 |
|  |  |  | ~1.78[d] | ~1.78[d] | 3.2–5.6[d] |  |

TABLE I-continued
NEUROLEPTIC ACTIVITY OF 1H-PYRIDO[4,3-b]INDOLES

Structures (A) and (B): 8-fluoro-5-(4-fluorophenyl)-pyrido[4,3-b]indole cores with N—(CH$_2$)$_n$R$^1$ substituent.

| A/B | R$^1$ | n | Amphetamine Activity$^{(b)}$ (approx. ED$_{50}$ mg/kg i.p.) 1 hr. | 5 hr. | 24 hr. | Inhibition H$^3$-Spiroperidol Binding$^{(c)}$ IC$_{50}$ (nM) |
|---|---|---|---|---|---|---|
| (A) | —N\_\_NH (piperazinyl) | 4 | >10 | 1–3.2 | >10 | 15 |
| (A) | —N\_\_NCOCH$_3$ | 2 | 0.18 | 0.06 | 0.57 | 25 |
|     |   | 4 | 1–3.2 | 0.32–1.0 | 0.32–1.0 | 17 |
|     |   | 2(+) | 0.04 | 0.02 | 0.23 | 23 |
| (A) | —N\_\_N—CH$_2$C$_6$H$_5$ | 4 | 3.2–10 | ~3.2 | 3.2–10 | 32 |
| (B) | —NHCOCH$_3$ | 6 | 0.32–1.0 | 0.32–1.0 | >10 | 8.8 |
| (B) | 2-piperidon-1-yl | 4 | ~1 | ~3.2 | >10 | 4.0 |
| (B) | —NHCOOC$_2$H$_5$ | 6 | 1–3.2 | ~3.2 | >10 | 6.8 |
| Chlorpromazine | | | 5.3 | 8.5 | >32 | 51 |

$^{(a)}$Unless otherwise indicated by (+) or (−), the compound tested was the racemic (±) variant.
$^{(b)}$Entries are ranges within which fall the ED$_{50}$ values for blocking hyperactivity and stereotypy induced by amphetamine. Details are given in the text.
$^{(c)}$IC$_{50}$ values were estimated graphically usually using four drug concentrations separated by 0.5 log unit. Entries are generally means of two or three determinations. For details, see the text.
$^{(d)}$Oral dosage.

EXAMPLE 1
1-(4-Chloro-1-butyl)-2-piperidone

Sodium hydride (3.87 g of 50% dispersion in oil, 0.0807 mole) was suspended and stirred in 80 ml of dry dimethylformamide. A solution of 1,4-dichlorobutane (44 ml, 0.404 mole) and 2-piperidone (8 g, 0.0807 mole) in 100 ml of dimethylformamide was added dropwise over 1 hour, maintaining the temperature at 25°–30° C. by use of a water bath. The reaction mixture was stirred for 16 hours at room temperature, then byproduct salt removed by filtration and the mother liquor evaporated in vacuo to one-tenth volume. The resulting concentrate was distributed between 100 ml of water and 100 ml of hexane. The lower, oily phase of three phases was separated, diluted with 50 ml of methylene chloride, dried over magnesium sulfate, filtered and evaporated to yield 1-(4-chloro-1-butyl)-2-piperidone as an oil [14.3 g; pnmr(CDCl$_3$) delta 1.4–1.83 (4H, m), 3.03–3.72 (6H, m), 4.10–4.43 (2H, t, J=7)].

In like manner, 1,2-dichloroethane, 1,3-dichloropropane, 1,5-dichloropentane, 1,4-dichloro-2-butene and 1,4-dichloro-2-butyne are reacted with 2-piperidone to yield respectively, 1-(2-chloroethyl)-2-piperidone, 1-(3-chloro-1-propyl)-2-piperidone, 1-(5-chloro-1-pentyl)-2-piperidone, 1-(4-chloro-2-buten-1-yl)-2-piperidone, 1-(4-chloro-2-butyn-1-yl)-2-piperidone.

In like manner, 6-chloro-1-hexanol is reacted with 2-piperidone to produce 1-(6-hydroxy-1-hexyl)-2-piperidone. The latter is reacted with methanesulfonyl chloride in methylene chloride in the presence of one equivalent of triethylamine to yield 1-(6-methanesulfonyloxy-1-hexyl)-2-piperidone.

In like manner, 1,4-dichlorobutane is reacted with 2-pyrrolidinone, 6-hexanelactam (epsilon-caprolactam) and 1,2,3,4-tetrahydro-2-benzo[b]pyridone to produce respectively, 1-(4-chloro-1-butyl)-2-pyrrolidinone, N-(4-chloro-1-butyl)-6-hexanelactam and 1-(4-chloro-1-butyl)-1,2,3,4-tetrahydro-2-benzo[b]pyridone.

In like manner, 2-hydroxypyrrole (tautomeric equivalent form of 2-pyrrolin-5-one) and 2-hydroxyindole are reacted with 1,4-dichlorobutane to produce respectively, 1-(4-chloro-1-butyl)-2-hydroxypyrrole and 1-(4-chloro-1-butyl)-2-hydroxyindole.

EXAMPLE 2
(±)-8-Fluoro-5-(4-fluorophenyl)-2-[4-(2-piperidon-1-yl)-1-butyl]-2,3,4,4a,5,9b-hexahydro-4a,9b-trans-1H-pyrido[4,3-b]indole Hydrochloride (Method A)

1-(4-Chloro-1-butyl)-2-piperidone (496 mg, 2.62 mmole), (±)-8-fluoro-5-(4-fluorophenyl)-2,3,4,4a,5,9b-hexahydro-4a,9b-trans-1H-pyrido[4,3-b]indole (500 mg, 1.75 mmole), anhydrous sodium carbonate (1.1 g, 10.4 mmole) and potassium iodide (5 mg) were combined in 3-methyl-2-butanone (20 ml) and the slurry refluxed for 16 hours. The reaction mixture was evaporated in vacuo to solids, and the residue partitioned between 50 ml of methylene chloride and 50 ml of water. The aqueous phase was washed with 50 ml of fresh methylene chloride. The organic layers were combined, dried over anhydrous magnesium sulfate, filtered and evaporated to a gum. The gum was chromatographed on silica gel with 1:10 methanol:ethyl acetate as eluant and tlc monitoring. Clean product-containing fractions were combined and evaporated to a second gum. The second gum as taken into methylene chloride, converted to hydrochloride salt by the addition of ethereal hydrogen chloride, and the mixture reevaporated to a foam. The foam was slurried with 50 ml of ether and filtered to yield the title product [532 mg, Rf 0.4 (1:4 methanol:ethyl acetate); ir(KBr) 1215, 1468, 1503, 1605, 2924, 3394 cm$^{-1}$].

In like manner, 1-(2-chloroethyl)-2-piperidone, 1-(3-chloro-1-propyl)-2-piperidone, 1-(5-chloro-1-pentyl)-2-piperidone, 1-(6-methanesulfonyloxy-1-hexyl)-2-piperidone, 1-(4-chloro-1-butyl)-2-pyrrolidinone, N-(4-chloro-1-butyl)-6-hexanelactam, 1-(4-chloro-1-butyl)-1,2,3,4-tetrahydro-2-benzo[b]pyridone, 1-(4-chloro-2-buten-1-yl)-2-piperidone and 1-(4-chloro-2-butyn-1-yl)-2-piperidone of the preceding Example are converted, respectively, to:

(±)-8-fluoro-5-(4-fluorophenyl)-2-[2-(2-piperidon-1-yl)ethyl]-2,3,4,4a,5,9b-hexahydro-4a,9b-trans-1H-pyrido[4,3-b]indole hydrochloride;

(±)-8-fluoro-5-(4-fluorophenyl)-2-[3-(2-piperidon-1-yl)-1-propyl]-2,3,4,4a,5,9b-hexahydro-4a,9b-trans-1H-pyrido[4,3-b]indole hydrochloride;

(±)-8-fluoro-5-(4-fluorophenyl)-2-[5-(2-piperidon-1-yl)-1-pentyl]-2,3,4,4a,5,9b-hexahydro-4a,9b-trans-1H-pyrido[4,3-b]indole hydrochloride;

(±)-8-fluoro-5-(4-fluorophenyl)-2-[5-(2-piperidon-1-yl)-1-hexyl]-2,3,4,4a,5,9b-hexahydro-4a,9b-trans-1H-pyrido[4,3-b]indole hydrochloride;

(±)-8-fluoro-5-(4-fluorophenyl)-2-[4-(2-pyrrolidinon-1-yl)-1-butyl]-2,3,4,4a,5,9b-hexahydro-4a,9b-trans-1H-pyrido[4,3-b]indole hydrochloride;

(±)-8-fluoro-5-(4-fluorophenyl)-2-[4-(2-perhydroazepinon-1-yl)-1-butyl]-2,3,4,4a,5,9b-hexahydro-4a,9b-trans-1H-pyrido[4,3-b]indole hydrochloride;

(±)-8-fluoro-5-(4-fluorophenyl)-2-[4-(1,2,3,4-tetrahydro-2-benzo[b]pyridon-1-yl)-1-butyl]-2,3,4,4a,5, 9b-hexahydro-4a,9b-trans-pyrido[4,3-b]indole;

(±)-8-fluoro-5-(4-fluorophenyl)-2-[4-(2-piperidon-1-yl)-2-buten-1-yl]-2,3,4,4a,5,9b-hexahydro-4a,9b-trans-1H-pyrido[4,3-b]indole hydrochloride; and (±)-8-fluoro-5-(4-fluorophenyl)-2-[4-(2-piperidon-1-yl)-2-butyn-1-yl]-2,3,4,4a,5,9b-hexahydro-4a,9b-trans-1H-pyrido[4,3-b]indole hydrochloride.

In like manner, 1-(4-chloro-1-butyl)-2-hydroxypyrrole and 1-(4-chloro-1-butyl)-2-hydroxyindole of Example 1 are converted, respectively, to:

(±)-8-fluoro-5-(4-fluorophenyl)-2-[4-(2-hydroxy-1-pyrrolyl)-1-butyl]-2,3,4,4a,5,9b-hexahydro-4a,9b-trans-1H-pyrido[4,3-b]indole; and (±)-8-fluoro-5-(4-fluorophenyl)-2-[4-(2-hydroxy-1-indolyl)-1-butyl]-2,3,4,4a,5,9b-hexahydro-4a,9b-trans-1H-pyrido[4,3-b]indole.

The last two named compounds are tautomeric forms, respectively, of:

(±)-8-fluoro-5-(4-fluorophenyl)-2-[4-(2-pyrrolin-5-on-1-yl)-1-butyl]-2,3,4,4a,5,9b-hexahydro-4a,9b-trans-1H-pyrido[4,3-b]indole; and (±)-8-fluoro-5-(4-fluorophenyl)-2-[4-(2,3-dihydro-2-indolon-1-yl)-1-butyl]-2,3,4,4a,5,9b-hexahydro-4a,9b-trans-1H-pyrido[4,3-b]indole.

In like manner, 1-(4-chloro-1-butyl)-2-piperidone is reacted with the appropriately substituted 5-phenyl-2,3,4,4a,5,9b-hexahydro-4a,9b-trans-1H-pyrido[4,3-b]indole to prepare:

(+)-5-phenyl-2-[4-(2-piperidon-1-yl)-1-butyl]-2,3,4,4a,5,9b-hexahydro-4a,9b-trans-1H-pyrido[4,3-b]-indole;

(+)-8-fluoro-5-(4-fluorophenyl)-2-[4-(2-piperidon-1-yl)-1-butyl]-2,3,4,4a,5,9b-hexahydro-4a,9b-trans-1H-pyrido[4,3-b]indole;

(+)-8-fluoro-5-(3-fluorophenyl)-2-[4-(2-piperidon-1-yl)-1-butyl]-2,3,4,4a,5,9b-hexahydro-4a,9b-trans-1H-pyrido[4,3-b]indole;

(+)-5-(2-fluorophenyl)-2-[4-(2-piperidon-1-yl)-1-butyl]-2,3,4,4a,5,9b-hexahydro-4a,9b-trans-1H-pyrido[4,3-b]indole;

(±)-8-chloro-5-(4-chlorophenyl)-2-[4-(2-piperidon-1-yl)-1-butyl]-2,3,4,4a,5,9b-hexahydro-4a,9b-trans-1H-pyrido[4,3-b]indole; and (±)-5-(3-methoxyphenyl)-2-[4-(2-piperidon-1-yl)-1-butyl]-2,3,4,4a,5,9b-hexahydro-4a,9b-trans-1H-pyrido[4,3-b]indole.

(±)-8-chloro-5-(4-fluorophenyl)-2-[4-(2-piperidon-1-yl)-1-butyl]-2,3,4,4a,5,9b-hexahydro-4a,9b-trans-1H-pyrido[4,3-b]indole;

(+)-8-bromo-5-(4-bromophenyl)-2-[4-(2-piperidon-1-yl)-1-butyl]-2,3,4,4a,5,9b-hexahydro-4a,9b-trans-1H-pyrido[4,3-b]indole;

(+)-8-methyl-5-phenyl-2-[4-(2-piperidon-1-yl)-1-butyl]-2,3,4,4a,5,9b-hexahydro-4a,9b-trans-1H-pyrido[4,3-b]indole;

(+)-8-fluoro-5-(2-methoxyphenyl)-2-[4-(2-piperidon-1-yl)-1-butyl]-2,3,4,4a,5,9b-hexahydro-4a,9b-trans-1H-pyrido[4,3-b]indole;

(+)-8-fluoro-5-(3-methylphenyl)-2-[4-(2-piperidon-1-yl)-1-butyl]-2,3,4,4a,5,9b-hexahydro-4a,9b-trans-1H-pyrido[4,3-b]indole; and (+)-8-fluoro-5-(4-methyl-2-methoxyphenyl)-2-[4-(2-piperidon-1-yl)-1-butyl]-2,3,4,4a,5,9b-hexahydro-4a,9b-trans-1H-pyrido[4,3-b]indole.

EXAMPLE 3

(+)-8-Fluoro-5-(4-fluorophenyl)-2-[4-(2-piperidon-1-yl)-2-butyn-1-yl]-2,3,4,4a,5,9b-hexahydro-4a,9b-trans-1H-pyrido[4,3-b]indole Sodium hydride (5.76 g of 50% dispersion in oil, 0.12 mole) was washed three times with hexane and suspended in 645 ml of toluene. 2-Piperidone (11.88 g, 0.12 mole) in 100 ml of toluene was added to the well stirred sodium hydride suspension and heated to reflux for 2 hours. The reaction mixture was cooled to 15° C. and 2-propynyl bromide (14.28 g, 0.12 mole) in 55 ml of toluene added over 30 minutes. The mixture was then stirred at room temperature for 19 hours, filtered and mother liquor evaporated to yield a first batch of 1-(2-propynyl)-2-piperidone as an oil (7.87 g of about 55% purity by pnmr assay).

In a second run the level of sodium hydride dispersion was increased to 7.2 g, suspended in 500 ml of tetrahydrofuran rather than toluene. For isolation, the reaction mixture was poured cautiously onto a mixture of concentrated hydrochloric acid (17 ml, 0.20 mole) and 300 ml of ice. The quenched reaction mixture was extracted with three portions of ethyl acetate. The organic extracts were combined, dried over anhydrous magnesium sulfate, filtered and evaporated to yield a second batch of 1-(2-propynyl)-2-piperidone (13 g of about 50% purity by pnmr assay).

(+)-8-Fluoro-5-(3-fluorophenyl)-2,3,4,4a,5,9b-hexahydro-4a,9b-trans-1H-pyrido[4,3-b]indole hydrochloride (11.0 g, 34.2 mmoles) was converted to free base by distribution between ethyl acetate and excess dilute sodium hydroxide. The ethyl acetate layer was separated, dried over anhydrous magnesium sulfate, filtered and evaporated to dryness in vacuo. The resulting gum was dissolved in 450 ml of absolute ethanol. Formaldehyde (3.41 ml of 30% in water, 34.2 mmoles) was added and the stirred solution warmed to 35° C. Cuprous chloride (5.1 g) and then a mixture of first and second batches of 1-(2-propynyl)-2-piperidone (4.67 g by assay, 34.2 mmoles) were added. The resulting suspension was stirred for 18 hours at room temperature. The reaction mixture was clarified by filtration with ethanol wash and the combined filtrate/wash evaporated to a gum. The gum was dissolved in the minimum volume of 9:1 ethyl acetate:methanol and chromatographed on 650 g of silica gel with first ethyl acetate and then 9:1 ethyl acetate:methanol as eluant, and monitoring by tlc. Clean middle cuts were combined and evaporated to dryness to yield the title product [12.5 g; Rf 0.75 (1:10 ethyl acetate:methanol)] in the form of its free base. A portion of this free base (0.5 g) was dissolved in 50 ml of ether. The stirred solution was saturated with hydrogen chloride and left to stand for two days. The title product was recovered as crystalline solid by filtration [247 mg, m.p. 123°–125° C., [alpha]$_D^{25}$ = +13.78° (methanol, c=0.73)].

Analysis: Calcd. for $C_{26}H_{27}ON_3F_2.HCl.1.5\ H_2O$: C, 62.57; H, 6.26; N, 8.42. Found: C, 62.37; H, 6.25; N, 8.20.

EXAMPLE 4

(+)-8-Fluoro-5-(4-fluorophenyl)-2-[4-(2-piperidon-1-yl)-1-butyl]-2,3,4,4a,5,9b-hexahydro-4a,9b-trans-1H-pyrido[4,3-b]indole (Method B)

Free base form of the compound of the preceding Example (12.4 g) was dissolved in 270 ml of absolute ethanol. Catalyst (5% Pd/C, 3 g) was added and the mixture hydrogenated at room temperature for 90 minutes, in which time uptake of hydrogen was complete. Catalyst was recovered by filtration and the filtrate evaporated to a gum. The gum was chromatographed on 250 g of silica gel with 9:1 ethyl acetate:methanol as eluant and monitoring by tlc. Clean product-containing fractions were evaporated to yield the title product [8.6 g, Rf 0.3 (9:1 ethyl acetate:methanol); [alpha]$_D^{23}$ = +15.8° (methanol, c=0.5)] as the free base. Free base (87 mg) and benzenesulfonic acid (35 mg) gave the benzene sulfonate salt of the title product (84 mg, m.p. 138°–141° C.). Free base (85 mg) and benzoic acid (26 mg) similarly gave the benzoate salt (m.p. 42°–44° C.) and maleic acid similarly gave a meleate salt (m.p. ca 80° C.).

In like manner, (±)-8-fluoro-5-(4-fluorophenyl)-2-[4-(2-piperidon-1-yl)-2-buten-1-yl]-2,3,4,4a,5,9b-hexahydro-4a,9b-trans-1H-pyrido[4,3-b]indole hydrochloride is hydrogenated to (±)-8-fluoro-5-(4-fluorophenyl)-2-[4-(2-piperidon-1-yl)-1-butyl]-2,3,4,4a,5,9b-hexahydro-4a,9b-trans-1H-pyrido[4,3-b]indole.

EXAMPLE 5

(+)-8-Fluoro-5-(4-fluorophenyl)-2-[4-(2-piperidon-1-yl)-1-butyl]-2,3,4,4a,5,9b-hexahydro-4a,9b-trans-1H-pyrido[4,3-b]indole Bis(dihydrogenphosphate)

Free base form of the title compound (7.2 g, 16.4 mmoles) was dissolved in 200 ml of ethyl acetate. With strong stirring, phosphoric acid (3.76 g of 85.5%, 32.8 mmoles) in 20 ml of ethyl acetate was added dropwise, precipitating the desired salt in crude form (12 g). The crude was dissolved in 50 ml of boiling methanol. Ethyl acetate (50 ml) was added and the mixture cooled slowly to room temperature. Purified title product was recovered by filtration and dried in vacuo over phosphorus pentoxide (8.49 g, m.p. 197°–8° C.; [alpha]$_D^{23}$ = +16.61°).

Analysis: Calcd. for $C_{26}H_{31}ON_3F_2.(H_3PO_4)_2$: C, 49.14; H, 5.87; N, 6.62. Found: C, 48.93; H, 5.84; N, 6.68.

EXAMPLE 6

1-(6-Bromo-1-hexyl)-2-piperidone

Following the procedure of Example 1, sodium hydride (3.63 g of 50% dispersion in oil, 0.15 mole), 1,6-dibromohexane (23.07 ml, 0.15 mole) and 2-piperidone (7.5 g, 0.076 mole) were reacted in dimethylformamide. The filtered, concentrated reaction mixture was taken up in 200 ml of water and 200 ml of hexane. The hexane layer was separated and evaporated to an oil. The oil was chromatographed on silica gel using ethyl acetate as eluant and tlc monitoring. Clean product-containing fractions were combined and evaporated to yield 1-(6-bromo-1-hexyl)-2-piperidone as an oil (3.66 g).

In like manner 3-bromo-1-chloropropane, 1,3-dibromopropane, 1-bromo-4-chlorobutane, 1,4-dibromobutane, 1,4-dibromo-2-butene, 1,5-dibromopentane, 1,7-dibromoheptane, 1,8-dibromooctane and 1,9-dibromononane are reacted with 2-piperidone to yield, respectively, 1-(3-bromo-1-propyl)-2-piperidone, 1-(4-chloro-1-butyl)-2-piperidone, 1-(4-bromo-1-butyl)-2-piperidone, 1-(5-bromo-1-pentyl)-2-piperidone, 1-(7-bromo-1-heptyl)-2-piperidone, 1-(8-bromo-1-octyl)-2-piperidone and 1-(9-bromo-1-nonyl)-2-piperidone.

EXAMPLE 7

(±)-8-Fluoro-5-(4-fluorophenyl)-2-[6-(2-piperidon-1-yl)-1-hexyl]-2,3,4,4a,5,9b-hexahydro-4a,9b-trans-1H-pyrido[4,3-b]indole Hydrochloride (Method A)

Free base of the title product was prepared in crude form from 1-(6-bromo-1-hexyl)-2-piperidone by the procedure of Example 1, but on twice the scale. Purification was achieved by chromatography on silica gel with 1:9 methanol:ethyl acetate as eluant. Product fractions were combined, diluted with excess ethereal hydrogen chloride and evaporated to yield the title product as a solid (1.4 g).

Analysis: Calcd. for $C_{28}H_{35}ON_3F_2.HCl.0.75\ H_2O$: C, 64.97; H, 7.34; N, 8.11. Found: C, 64.84; H, 7.04; N, 7.96.

In like manner, 1-(3-bromo-1-propyl)-2-piperidone, 1-(4-chloro-1-butyl)-2-piperidone and 1-(4-bromo-1-butyl)-2-piperidone, 1-(5-bromo-1-pentyl)-2-piperidone, 1-(7-bromo-1-heptyl)-2-piperidone, 1-(7-bromo-1-octyl)-2-piperidone, and 1-(7-bromo-1-nonyl)-2-piperidone are converted, respectively, to:

(±)-8-fluoro-5-(4-fluorophenyl)-2-[3-(2-piperidon-1-yl)-1-propyl]-2,3,4,4a,5,9b-hexahydro-4a,9b-trans-1H-pyrido[4,3-b]indole hydrochloride;
(±)-8-fluoro-5-(4-fluorophenyl)-2-[4-(2-piperidon-1-yl)-1-butyl]-2,3,4,4a,5,9b-hexahydro-4a,9b-trans-1H-pyrido[4,3-b]indole hydrochloride;
(±)-8-fluoro-5-(4-fluorophenyl)-2-[5-(2-piperidon-1-yl)-1-pentyl]-2,3,4,4a,5,9b-hexahydro-4a,9b-trans-1H-pyrido[4,3-b]indole hydrochloride;
(±)-8-fluoro-5-(4-fluorophenyl)-2-[7-(2-piperidon-1-yl)-1-heptyl]-2,3,4,4a,5,9b-hexahydro-4a,9b-trans-1H-pyrido[4,3-b]indole hydrochloride;
(±)-8-fluoro-5-(4-fluorophenyl)-2-[8-(2-piperidon-1-yl)-1-octyl]-2,3,4,4a,5,9b-hexahydro-4a,9b-trans-1H-pyrido[4,3-b]indole hydrochloride; and
(±)-8-fluoro-5-(4-fluorophenyl)-2-[9-(2-piperidon-1-yl)-1-nonyl]-2,3,4,4a,5,9b-hexahydro-4a,9b-trans-1-H-pyrido[4,3-b]indole hydrochloride.

EXAMPLE 8

(±)-8-Fluoro-5-(4-fluorophenyl)-2-(4-chloro-1-butyl)-2,3,4,4a,5,9b-hexahydro-4a,9b-trans-1H-pyrido[4,3-b]indole Hydrochloride 4-Chlorobutyryl chloride (1.0 g, 7.1 mmoles), (±)-8-fluoro-5-(4-fluorophenyl)-2,3,4,4a,5,9b-hexahydro-4a,9b-trans-1H-pyrido[4,3-b]indole (2 g, 7 mmoles), and anhydrous sodium carbonate (1.5 g) are combined in 80 ml of 2-butanone and stirred at room temperature for 2 hours. The reaction mixture is evaporated to dryness and the residue distributed between 200 ml of methylene chloride and 200 ml of water. The water phase is washed with additional methylene chloride. The combined organic layers are evaporated to yield (±)-8-fluoro-5-(4-fluorophenyl)-2-(4-chlorobutyryl)-2,3,4,4a,5,9b-hexahydro-4a,9b-trans-1H-pyrido[4,3-b]indole. The latter is added to a stirred suspension of lithium aluminum hydride (0.19 g, 5 mmoles) in 35 ml of diethyl ether, keeping the temperature 25°–30° C. by the rate of addition. After stirring for 4 hours at room temperature, Glauber's salt (Na$_2$SO$_4$.10 H$_2$O; 1.5 g, 5 mmoles) is added portionwise over a 10 minute period. The mixture is filtered, and the filtrate acidified with ethereal hydrogen chloride and evaporated to yield the title product (hydrochloride salt). Free base, when desired, is regenerated immediately before use.

The corresponding 4-bromo-1-butyl derivative is prepared in like manner by substituting an equivalent amount of 4-bromobutyryl chloride in the first step of this two-step process.

EXAMPLE 9

(±)-8-Fluoro-5-(4-fluorophenyl)-2-[4-(2-piperidon-1-yl)-1-butyl]-2,3,4,4a,5,9b-hexahydro-4a,9b-trans-1H-pyrido[4,3-b]indole Hydrochloride (Method C)

At room temperature, sodium hydride (0.39 g of 50% dispersion in oil, 8.1 mmoles) is suspended and stirred in 8 ml of dimethylformamide. 2-Piperidone (0.8 g, 8.1 mmoles) in 5 ml of dimethylformamide is added dropwise over 1 hour. Then (±)-8-fluoro-5-(4-fluorophenyl)-2-(4-chloro-1-butyl)-2,3,4,4a,5,9b-hexahydro-4a,9b-trans-1H-pyrido[4,3-b]indole (2.97 g, 7.9 mmoles) in 5 ml of dimethylformamide is added over 5 minutes and the resulting mixture stirred for 48 hours at room temperature. Salts are removed by filtration and the mother liquor evaporated to dryness in vacuo. The crude product is further purified according to the methods detailed in Example 2.

In like manner, the corresponding 4-bromobutyl derivative of the preceding Example is also converted to the title product.

EXAMPLE 10

8-Fluoro-5-(4-fluorophenyl)-2-(3-cyano-1-propyl)-2,3,4,4a,5,9b-hexahydro-4a,9b-trans-1H-pyrido[4,3-b]indole A stirred suspension of 8-fluoro-5-(4-fluorophenyl)-2,3,4,4a,5,9b-hexahydro-4a,9b-trans-1H-pyrido[4,3-b]-indole (1 g, 3.49 mmoles), 4-bromobutanenitrile (0.723 g, 4.88 mmoles), anhydrous sodium carbonate (2.1 g, 20.9 mmoles), potassium iodide (0.289 g, 1.74 mmoles) in methylisobutylketone (40 ml) was refluxed under nitrogen for 16 hours. The reaction mixture was cooled to room temperature and evaporated in vacuo to dryness. The resulting white solid was partitioned between water (40 ml) and chloroform (50 ml). The phases were separated and the aqueous phase extracted with chloroform (50 ml). The organic layers were combined, dried (MgSO$_4$), and evaporated in vacuo to give a pale yellow oil. Treatment of the oil with hydrogen chloride gas in acetone (40 ml) gave upon filtration and washing with acetone (10 ml) 0.813 g, (60% yield) of the above titled nitrile intermediate as a white solid, m.p. 245°–249° C. (HCl salt).

Analysis: Calcd. for C$_{21}$H$_{21}$N$_3$F$_2$.HCl: C, 64.67; H, 5.42; N, 10.77. Found: C, 64.38; H, 5.71; N, 10.71.

EXAMPLE 11

(±)-8-Fluoro-5-(4-fluorophenyl)-2-(4-amino-1-butyl)-2,3,4,4a,5,9b-hexahydro-4a,9b-trans-1H-pyrido[4,3-b]indole Hydrochloride To a stirred suspension of lithium aluminum hydride (0.167 g, 4.4 mmoles) in diethyl ether (35 ml), under nitrogen, was added the nitrile intermediate of the preceding Example (0.781 g, 2.0 mmoles) at a rate sufficient to maintain the reaction temperature 28°–30° C. (15 minutes). After stirring for 4 hours at ambient temperature, Glauber's salt (Na$_2$SO$_4$.10 H$_2$O; 1.2 g, 4 mmoles) was added portionwise over a 10 minute period. The white solid was filtered and washed with diethyl ether (10 ml) and the filtrate evaporated in vacuo to give a pale yellow oil. Treatment of the oil with hydrogen chloride in ether (35 ml) gave upon filtration and washing with ether (20 ml), 0.498 g, (64% yield) of the above titled compound as a white solid m.p. 224°–227° C. (HCl salt).

Analysis: Calcd. for C$_{21}$H$_{25}$N$_3$F$_2$.2.5 H$_2$O.HCl: C, 53.28; H, 6.38; N, 8.87. Found: C, 52.98; H, 5.94; N, 8.66.

EXAMPLE 12

(±)-8-Fluoro-5-(4-fluorophenyl)-2-[4-(5-chlorovaleramido)-1-butyl]-2,3,4,4a,5,9b-hexahydro-1H-pyrido[4,3-b]indole The amine of the preceding Example (3.15 g, 8.03 mmoles) and triethylamine (4.4 ml, 32 mmoles) are dissolved in methylene chloride (100 ml), under nitrogen at 2° C. (ice bath). 5-Chlorovaleryl chloride (13.6 g, 8.8 mmoles) in 5 ml methylene chloride is added at a rate sufficient to maintain the reaction temperature 2°–5° C. After stirring at ambient temperature for 2 hours, the reaction mixture is poured onto saturated sodium bicarbonate solution (30 ml). The phases are separated and the aqueous phase extracted with methylene chloride (30 ml). The organic layers are combined, dried (MgSO4), and evaporated to dryness in vacuo to yield the title product.

EXAMPLE 13

(±)-8-Fluoro-5-(4fluorophenyl)-2-[4-(2-piperidon-1-yl]-1-butyl]-2,3,4,4a,5,9b-hexahydro-4a,9b-trans-1H-pyrido[4,3-b]indole Hydrochloride (Method D)

Sodium hydride (0.38 g of 50% dispersion in oil, 7.9 mmoles) is suspended and stirred in 8 ml of dimethylformamide and added dropwise to a solution of the chlorovaleramide of the preceding Example (3.75 g, 7.9 mmoles) in 12 ml of dimethylformamide. The mixture is stirred at ambient temperature for 48 hours, filtered and the mother liquor evaporated to dryness to yield crude title product. The crude is purified by the methods detailed in Example 2.

EXAMPLE 14

Ethyl (±)-5-[[4-[8-Fluoro-5-(4-fluorophenyl)-2,3,4,4a,5,9-hexahydro-4a,9b-trans-1H-pyrido[4,3-b]indol-2-yl-1-butylamino]valerate 8-Fluoro-5-(4-fluorophenyl)-2-(4-bromo-1-butyl)-2,3,4,4a,5,9-hexahydro-4a,9b-trans-1H-pyrido[4,3-b]indole (4.2 g, 10 mmoles) is dissolved in 35 ml of dimethyl formamide and added dropwise over 8 hours to a solution of ethyl 5-aminovalerate (6.5 g, 50 mmoles) in 35 ml of the same solvent maintained at 35° C. After maintaining for an additional 4 hours at this temperature, the reaction mixture is evaporated to dryness in vacuo. The residue is chased with additional dimethylformamide and pumped under high vacuum in a rotating evaporator to remove excess ethyl 5-aminovalerate to yield the title product.

EXAMPLE 15

(±)-8-Fluoro-5-(4-fluorophenyl)-2-[4-(2-piperidon-1-yl]-1-butyl]-2,3,4,4a,5,9b-hexahydro-4a,9b-trans-1H-pyrido[4,3-b]indole Hydrochloride (Method E)

The ethyl ester of the preceding Example (4.7 g, 10 mmoles) is taken up in 200 ml of methyl isobutyl ketone. Anhydrous sodium carbonate (10.6 g, 0.1 mole) is added, and the mixture refluxed for 16 hours. The title product is isolated and purified according to the methods of Example 2.

EXAMPLE 16

3-(4-Chloro-1-butyl)-2-oxazolidinone

Following the procedure of Piper et al. [J. Het. Chem. 4, p. 298 (1967)], sodium hydride (4.8 g of 50% dispersion in oil, 0.1 mole) was washed with pentane and suspended in 20 ml of dimethylformamide. A solution of 2-oxazolidinone (8.7 g, 0.10 mole) and 1,4-dichlorobutane (66 g, 0.52 mole) in 100 ml of dimethylformamide was then added dropwise over 30 minutes, maintaining the reaction temperature at 25°–30° C. The reaction was stirred for 18 hours at ambient temperature, then evaporated to an oil, and the oil taken up in ethyl acetate, treated with activated carbon, filtered over diatomaceous earth, and reevaporated in vacuo to yield the title product as an oil [16.5 g, contaminated with mineral oil from incompletely washed sodium hydride; pnmr/CDCl3/delta: 0.67–1.0 and 1.03–1.4 (mineral oil), 1.4–1.83 (m, 4H), 3.03–3.72 (m, 6H), 4.10–4.43 (t, 2H)].

In like manner, 1,3-dichloropropane and 1-chloro-3-bromopropane are each converted to 3-(3-chloro-1-propyl)-2-oxazolidinone, and 1,5-dichloropentane is converted to 3-(5-chloro-1-pentyl)-2-oxazolidinone.

In like manner, 4-oxazolidinone, 2-thiazolidinone, 2-oxazolone, 2-thiazolone and 3-morpholone are converted, respectively, to 3-(4-chloro-1-butyl)-4-oxazolidinone, 3-(4-chloro-1-butyl)-2-thiazolidinone, 3-(4-chloro-1-butyl)-2-oxazolone, 3-(4-chloro-1-butyl)-2-thiazolone and 4-(4-chloro-1-butyl)-3-morpholone.

EXAMPLE 17

(±)8-Fluoro-5-(4-fluorophenyl)-2-[4-(2-oxazolidinon-3-yl)-1-butyl]-2,3,4,4a,5,9b-hexahydro-4a,9b-trans-1H-pyrido[4,3-b]indole Hydrochloride By the procedure of Example 2, 1-(4-chloro-1-butyl)-2-oxazolidinone (0.93 g, 5.2 mmole) and (±)-8-fluoro-5-(4-fluorophenyl)-2,3,4,4a,5,9b-hexahydro-4a,9b-trans-1H-pyrido[4,3-b]indole (1.0 g, 3.5 mmoles) were reacted in 40 ml of 3-methyl-2-butanone in the presence of sodium carbonate (1.46 g, 13.8 mmoles) to yield, without chromatography, the free base of the title product in the form of a gum. The gum was taken up in a mixture of 10 ml of 2-propanol and 10 ml of acetone and converted to the hydrochloride salt by the addition of excess ethereal hydrogen chloride. The title product slowly crystallized and was recovered by filtration [1.02 g; Rf 0.65 (7:1 ethyl acetate:methanol); ir(KBr) 1181, 1219, 1258, 1477, 1513, 1760 cm$^{-1}$].

In like manner, 3-(3-chloro-1-propyl)-2-oxazolidinone, 3-(5-chloro-1-pentyl)-2-oxazolidinone, 3-(4-chloro-1-butyl)-4-oxazolidinone, 3-(4-chloro-1-butyl)-2-oxazolone, 3-(4-chloro-1-butyl)-2-thiazolone, and 4-(4-chloro-1-butyl)-3-morpholone are converted, respectively, to:

(±)-8-fluoro-5-(4-fluorophenyl)-2-[3-(2-oxazolidinon-3-yl)-1-propyl]-2,3,4,4a,5,9b-hexahydro-4a,9b-trans-1H-pyrido[4,3-b]indole hydrochloride;

(±)-8-fluoro-5-(4-fluorophenyl)-2-[5-(2-oxazolidinon-3-yl)-1-pentyl]-2,3,4,4a,5,9b-hexahydro-4a,9b-trans-1H-pyrido[4,3-b]indole hydrochloride;

(±)-8-fluoro-5-(4-fluorophenyl)-2-[4-(4-oxazolidinon-3-yl)-1-butyl]-2,3,4,4a,5,9b-hexahydro-4a,9b-trans-1H-pyrido[4,3-b]indole hydrochloride;

(±)-8-fluoro-5-(4-fluorophenyl)-2-[4-(2-oxazolidinon-3-yl)-1-butyl]-2,3,4,4a,5,9b-hexahydro-4a,9b-trans-1H-pyrido[4,3-b]indole hydrochloride;

(±)-8-fluoro-5-(4-fluorophenyl)-2-[4-(2-thiazolon-3-yl)-1-butyl]-2,3,4,4a,5,9b-hexahydro-4a,9b-trans-1H-pyrido[4,3-b]indole hydrochloride; and (±)-8-fluoro-5-(4-fluorophenyl)-2-[4-(3-morpholon-4-yl)-1-butyl]-2,3,4,4a,5,9b-hexahydro-4a,9b-trans-1H-pyrido-[4,3-b]indole.

EXAMPLE 18

3-(6-Bromohexyl)-2-oxazolidinone

By the procedure of Example 1, sodium hydride (3.85 g of 50% dispersion in oil, 0.0804 mole), 1,6-dibromohexane (24.5 ml, 0.16 mole) and 2-oxazolidinone (7.0 g, 0.0804 mole) in dimethylformamide (180 ml total) were reacted and the reaction mixture concentrated to one tenth volume. Hexane (200 ml) was added, salts were removed by filtration, and the heavy, oily layer separated from the filtrate. This heavy layer was chromatographed on silica gel with ethyl acetate as eluant and tlc monitoring. Clean product-containing fractions were combined and evaporated to yield the title product as an oil [1.59 g; Rf 0.5 (ethyl acetate)].

EXAMPLE 19

(±)-8-Fluoro-5-(4-fluorophenyl)-2-[4-(2-oxazolidinon-3-yl)-1-butyl]-2,3,4,4a,5,9b-hexahydro-4a,9b-trans-1H-pyrido[4,3-b]indole Hydrochloride By the procedure of Example 2, 3-(6-bromo-1-hexyl)-2-oxazolidinone (1.59 g, 63.5 mmole) and the pyridoindole (0.91 g, 31.8 mmoles) were converted, without chromatography, to the free base form of the title product, isolated as a gum. The gum was taken up in 30 ml of acetone, excess ethereal hydrogen chloride was added, and the mixture evaporated to dry solids. The solids were repulped in a mixture of 30 ml of ethyl acetate and 5 ml of acetone to yield the title product in purified form (0.90 g).

Analysis: Calcd. for $C_{26}H_{31}O_2N_3F_2 \cdot HCl \cdot 0.75\ H_2O$: C, 61.77; H, 6.72; N, 8.31. Found: C, 61.72; H, 6.44; N, 8.02.

EXAMPLE 20

3-(4-Chloro-1-butyl)-2,3-dihydro-2-benz[d]oxazolone

By the procedure of Example 1, 2,3-dihydro-2-benz[d]-oxazolone ("2-benzoxazolinone", Aldrich Chemical Co., 5 g, 0.037 mole) was converted to the title product. The product was isolated by filtration of the reaction mixture to remove salts and evaporation in vacuo to an oil. The oil was extracted with hexane and further dried by vacuum evaporation (0.8 g).

EXAMPLE 21

(±)-8-Fluoro-5-(4-fluorophenyl)-2-[4-(2,3-dihydro-2-benz[d]-oxazolon-3-yl)-1-butyl]-2,3,4,4a,5,9b-hexahydro-4a,9b-trans-1H-pyrido-[4,3-b]indole Hydrochloride By the procedure of Example 2, the chlorobutyl compound of the preceding Example (0.79 g, 3.5 mmoles) was reacted with (±)-8-fluoro-5-(4-fluorophenyl)-2,3,4,4a,5,9b-hexahydro-4a,9b-trans-1H-pyridoindole (500 mg, 1.75 mmole). The reaction mixture was filtered and the filtrate evaporated to a first gum. This first gum was chromatographed on silica gel with ethyl acetate as eluant and tlc monitoring. Clean product fractions were combined and the free base form of the title product isolated as a second gum by evaporation in vacuo. The second gum was dissolved in ether and excess ethereal hydrogen chloride was added. The resulting slurry was evaporated to obtain the title product as a solid [0.72 g, Rf 0.6 (ethyl acetate)].

Analysis: Calcd. for $C_{23}H_{27}O_2N_3F_2 \cdot HCl \cdot 0.5\ H_2O$: C, 64.55; H, 5.56; N, 8.06. Found: C, 64.20; H, 5.02; N, 8.03.

EXAMPLE 22

(±)-8-Fluoro-5-(4-fluorophenyl)-2-[4-(4-imidazolin-2-on-1-yl)-1-butyl]-2,3,4,4a,5,9b-hexahydro-4a,9b-trans-1H-pyrido[4,3-b]indole (±)-8-Fluoro-5-(4-fluorophenyl)-2-(4-bromo-1-butyl)-2,3,4,4a,5,9b-hexahydro-4a,9b-trans-1H-pyrido[4,3-b]indole of Example 8 is reacted with 4-imidazolin-2-on (5 equivalents) by the procedure of Example 9, using 1 equivalent of sodium hydride. The product is isolated by partial evaporation in vacuo, removal of salts by filtration and evaporation of the filtrate to dryness in vacuo. Removal of excess 4-imidazolin-2-one is facilitated by several chases with dimethylformamide.

It is understood that the tautomeric equivalent of the title product is (±)-8-fluoro-5-(4-fluorophenyl)-2-[4-(2-hydroxy-1-imidazolyl)-1-butyl]-2,3,4,4a,5,9b-hexahydro-4a,9b-trans-pyrido[4,3-b]indole.

Substitution of the 5 equivalents of 4-imidazolin-2-one in this process with 1 to 1.1 equivalents of 1-methyl-4-imidazolin-2-one, 1-(2-pentyl)-4-imidazolin-2-one, 1-phenyl-4-imidazolin-2-one, 1-(4-fluorophenyl)-4-imidazolin-2-one, 1-(3-methoxyphenyl)-4-imidazolin-2-one, 1-(2-methylphenyl)-4-imidazolin-2-one, 1-benzyl-4-imidazolin-2-one, 1-(3-chlorobenzyl)-4-imidazolin-2-one, 1-(4-ethylbenzyl-4-imidazolin-2-one yields, respectively:

(±)-8-fluoro-5-(4-fluorophenyl)-2-[4-(3-methyl-4-imidazolin-2-on-1-yl)-1-butyl]-2,3,4,4a,5,9b-hexahydro-4a,9b-trans-1H-pyrido[4,3-b]indole;

(±)-8-fluoro-5-(4-fluorophenyl)-2-[[4-[3-(2-pentyl)-4-imidazolin-2-on-1-yl]-1-butyl]]-2,3,4,4a,5,9b-hexahydro-4a,9b-trans-1H-pyrido[4,3-b]indole;

(±)-8-fluoro-5-(4-fluorophenyl)-2-[4-(3-phenyl-4-imidazolin-2-on-1-yl)-1-butyl]-2,3,4,4a,5,9b-hexahydro-4a,9b-trans-1H-pyrido[4,3-b]indole;

(±)-8-fluoro-5-(4-fluorophenyl)-2-[[4-[3-(4-fluorophenyl)-4-imidazolin-2-on-1-yl]-1-butyl]]-2,3,4,4a,5,9b-hexahydro-4a,9b-trans-1H-pyrido[4,3-b]indole;

(±)-8-fluoro-5-(4-fluorophenyl)-2-[[4-[3-(3-methoxyphenyl)-4-imidazolin-2-on-1-yl]-1-butyl]]-2,3,4,4a,5,9b-hexahydro-4a,9b-trans-1H-pyrido[4,3-b]indole;

(±)-8-fluoro-5-(4-fluorophenyl)-2-[[4-[3-(2-methylphenyl)-4-imidazolin-2-on-1-yl]-1-butyl]]-2,3,4,4a,5,9b-hexahydro-4a,9b-trans-1H-pyrido[4,3-b]indole;

(±)-8-fluoro-5-(4-fluorophenyl)-2-[4-(3-benzyl-4-imidazolin-2-on-1-yl)-1-butyl]-2,3,4,4a,5,9b-hexahydro-4a,9b-trans-1H-pyrido[4,3-b]indole;

(±)-8-fluoro-5-(4-fluorophenyl)-2-[[4-[3-(3-chlorobenzyl)-4-imidazolin-2-on-1-yl]-1-butyl]]-2,3,4,4a,5,9b-hexahydro-4a,9b-trans-1H-pyrido[4,3-b]indole;

(±)-8-fluoro-5-(4-fluorophenyl)-2-[[4-[3-(4-ethylbenzyl)-4-imidazolin-2-on-1-yl]-1-butyl]]-2,3,4,4a,5,9b-hexahydro-4a,9b-trans-1H-pyrido[4,3-b]indole; and (±)-8-fluoro-5-(4-fluorophenyl)-2-[4-(3-methylimidazolidin-5-on-1-yl)-1-butyl]-2,3,4,4a,5,9b-hexahydro-4a,9b-trans-1H-pyrido[4,3-b]indole.

In like manner, 2-imidazolidinone, 1-methyl-2-imidazolidinone, 4-methyl-2-piperazinone, perhydro-2-pyrimidinone, 2,3-dihydrobenz[d]imidazol-2-one (tautomeric equivalent of 2-hydroxybenz[d]imidazole) and 4-oxazolidinone are converted, respectively, to:

(±)-8-fluoro-5-(4-fluorophenyl)-2-[4-(2-imidazolinon-1-yl)-1-butyl]-2,3,4,4a,5,9b-hexahydro-4a,9b-trans-1H-pyrido[4,3-b]indole;

(±)-8-fluoro-5-(4-fluorophenyl)-2-[4-(3-methyl-2-imidazolinon-1-yl)-1-butyl]-2,3,4,4a,5,9b-hexahydro-4a,9b-trans-1H-pyrido[4,3-b]indole;

(±)-8-fluoro-5-(4-fluorophenyl)-2-[4-(4-methyl-2-piperazinon-1-yl)-1-butyl]-2,3,4,4a,5,9b-hexahydro-4a,9b-trans-1H-pyrido[4,3-b]indole;

(±)-8-fluoro-5-(4-fluorophenyl)-2-[4-(perhydro-2-pyrimidinon-1-yl)-1-butyl]-2,3,4,4a,5,9b-hexahydro-4a,9b-trans-1H-pyrido[4,3-b]indole;

(±)-8-fluoro-5-(4-fluorophenyl)-2-[4-(2,3-dihydrobenz[d]imidazol-2-on-1-yl)-1-butyl]-2,3,4,4a,5,9b-hexahydro-4a,9b-trans-1H-pyrido[4,3-b]indole; and (±)-8-fluoro-5-(4-fluorophenyl)-2-[4-(oxazolidin-4-on-3-yl)-1-butyl]-2,3,4,4a,5,9b-hexahydro-4a,9b-trans-1H-pyrido[4,3-b]indole.

EXAMPLE 23

2-(4-Acetylpiperazino)ethanol

2-Piperazinoethanol (7.81 g, 60 mmoles) and triethylamine (8.36 ml, 66 mmoles) were dissolved in 100 ml of methylene chloride and cooled to 0°–5° C. Acetyl chloride (4.28 ml, 60 mmoles) in 20 ml of methylene chloride was added and the reaction mixture warmed to room temperature, held for 2 hours, and then evaporated in vacuo to dry solids. The solids were triturated with four portions of warm ether. The triturates were combined, dried over anhydrous magnesium sulfate, filtered and evaporated to yield 2-(4-acetylpiperazino)ethanol as an oil [7.5 g; free of triethylamine and triethylamine hydrochloride by pnmr assay; Rf 0.3 (methanol/10% acetic acid)].

In this process acetyl chloride is replaced by an equivalent of acetoformic acid reagent (cf Blackwood et al., J. Am. Chem. Soc. 82, pp. 5194-7 (1960)), isobutyryl chloride, valeryl chloride, benzoyl chloride, 4-methoxybenzoyl chloride, phenylacetyl chloride, 3-fluorophenylacetyl chloride, methanesulfonyl chloride, benzenesulfonyl chloride, p-toluenesulfonyl chloride, or 4-chlorobenzenesulfonyl chloride to produce, respectively, 2-(4-formylpiperazino)ethanol;
2-(4-isobutyrylpiperazino)ethanol;
2-(4-valerylpiperazino)ethanol;
2-(4-benzoylpiperazino)ethanol;
2-[4-(4-methoxybenzoyl)piperazino]ethanol;
2-(4-phenylacetylpiperazino)ethanol;
2-[4-(3-chlorophenylacetyl)piperazino]ethanol;
2-(4-methanesulfonylpiperazino)ethanol;
2-(4-benzenesulfonylpiperazino)ethanol;
2-[4-(p-toluenesulfonyl)piperazino]ethanol; and
2-[4-(4-chlorobenzenesulfonyl)piperazino]ethanol.

In the same process, 2-piperazinoethanol is replaced by a large excess of piperazine (e.g., 5 equivalents) and triethylamine is omitted to produce 1-acetylpiperazine.

In the same process, 2-piperazinoethanol is replaced by equivalent 2-(4-acetylpiperazino)ethanol and acetyl chloride is replaced by equivalent methanesulfonyl chloride to produce 2-(4-acetylpiperazino)ethyl mesylate.

EXAMPLE 24

2-(4-Acetylpiperazino)ethyl Chloride

Method A 2-(4-Acetylpiperazino)ethanol (3.0 g) was dissolved in 30 ml of methylene chloride and cooled to 0°–5° C. Excess thionyl chloride (10 ml) was added dropwise. Precipitation of some gum and solids was noted. The reaction mixture was then refluxed for 90 minutes by which time the precipitated materials had redissolved. The mixture was evaporated to dryness in vacuo. The resulting gum was taken up in 100 ml of acetone and insolubles removed by filtration. The acetone filtrate was evaporated to an oil which was crystallized from 1:2 ethanol:ethyl acetate and ether to yield purified 2-(4-acetylpiperazino)ethyl chloride.

In like manner, the other acylpiperazinoethanols of the preceding Example are converted to:

2-(4-formylpiperazino)ethyl chloride;
2-(4-isobutyrylpiperazino)ethyl chloride;
2-(4-valerylpiperazino)ethyl chloride;
2-(4-benzoylpiperazino)ethyl chloride;
2-[4-(4-methoxybenzoyl)piperazino]ethyl chloride;
2-(4-phenylacetylpiperazino)ethyl chloride;
2-[4-(3-chlorophenylacetyl)piperazino]ethyl chloride;
2-(4-methanesulfonylpiperazino)ethyl chloride;
2-(4-benzenesulfonylpiperazino)ethyl chloride;
2-[4-(p-toluenesulfonyl)piperazino]ethyl chloride; and
2-[4-(4-chlorobenzenesulfonyl)piperazino]ethyl chloride.

Method B

1-Acetylpiperazine (1.28 g, 10 mmoles), 1,2-dichloroethane (5 g, 50 mmoles), anhydrous sodium carbonate (2.5 g) and potassium iodide (25 mg) are combined in 40 ml of 3-methyl-2-butanone and refluxed for 16 hours. The reaction mixture is evaporated to dryness in vacuo and the residue distributed between 100 ml of water and 150 ml of methylene chloride. The methylene chloride layer is dried over anhydrous magnesium sulfate and evaporated to dryness to yield 2-(4-acetylpiperazino)-ethyl chloride.

In this process, substitution of 1,2-dichloroethane by 1,2-dibromoethane, 1,3-dichloropropane, 1,4-dibromobutane, 1-bromo-4-chlorobutane, 1,5-dibromopentane or 1,6-dibromohexane provides a method for the preparation of, respectively:

2-(4-acetylpiperazino)ethyl bromide;
3-(4-acetylpiperazino)propyl chloride;
4-(4-acetylpiperazino)butyl bromide;
4-(4-acetylpiperazino)butyl chloride;
5-(4-acetylpiperazino)pentyl bromide; and
6-(4-acetylpiperazino)hexyl bromide.

EXAMPLE 25

(±)-8-Fluoro-5-(4-fluorophenyl)-2-[2-(4-acetylpiperazino)-ethyl]-2,3,4,4a,5,9b-hexahydro-4a,9b-trans-1H-pyrido[4,3-b]indole Bis-hydrogen Maleate (±)-8-Fluoro-5-(4-fluorophenyl)-2,3,4,4a,5,9b-hexahydro-4a,9b-trans-1H-pyrido[4,3-b]indole (1.00 g, 3.50 mmole), 2-(4-acetylpiperazino)ethyl chloride (0.885 g, 3.90 mmole) and triethylamine (1.09 ml, 7.80 mmole) were combined in 75 ml of absolute ethanol and refluxed for 2 hours. The reaction mixture was then cooled to room temperature and evaporated to dryness in vacuo. The residue was distributed between water and ether and the water layer extracted with two portions of fresh ether. The combined ether layers were dried over anhydrous magnesium sulfate filtered and evaporated to yield a first crop of product. The earlier aqueous phase was made basic with 10% sodium hydroxide and extracted with two portions of fresh ether. The combined, dried ether extracts were likewise taken to dryness to yield a second crop of product, pumped under high vacuum to remove extraneous triethylamine. The first and second crops of product were combined and chromatographed on 30 g of silica gel with 1:1 ethyl acetate:methanol as eluant.

Clean product fractions were combined and evaporated to yield the title product as the free base (gum). The free base was taken into acetone and excess maleic acid added. The title product crystallized in two crops, which were combined and recrystallized from acetonitrile/methanol. Yield: 428 mg (m.p. 203.5°–204.5° C.; m/e 440).

Analysis: Calcd. for $C_{25}H_{30}ON_4F_2\cdot 2C_4H_4O_4$: C, 58.92; H, 5.69; N, 8.33. Found: C, 58.32; H, 5.60; N, 8.16.

In like manner, 2-(4-acetylpiperazino)ethyl bromide and 2-(4-acetylpiperazino)ethyl mesylate are reacted with the same pyridoindole substrate to produce the title product.

The same process, substituting 2-(4-acetylpiperazino)ethyl chloride with the appropriate chloride or bromide of the preceding Example, is used to prepare:

(±)-8-fluoro-5-(4-fluorophenyl)-2-[2-(4-formyl-piperazino)ethyl]-2,3,4,4a,5,9b-hexahydro-4a,9b-trans-1H-pyrido[4,3-b]indole;

(±)-8-fluoro-5-(4-fluorophenyl)-2-[2-(4-isobutyryl-piperazino)ethyl]-2,3,4,4a,5,9b-hexahydro-4a,9b-trans-1H-pyrido[4,3-b]indole;

(±)-8-fluoro-5-(4-fluorophenyl)-2-[2-(4-valeryl-piperazino)ethyl]-2,3,4,4a,5,9b-hexahydro-4a,9b-trans-1H-pyrido[4,3-b]indole;

(±)-8-fluoro-5-(4-fluorophenyl)-2-[2-(4-benzoyl-piperazino)ethyl]-2,3,4,4a,5,9b-hexahydro-4a,9b-trans-1H-pyrido[4,3-b]indole;

(±)-8-fluoro-5-(4-fluorophenyl)-2-[[2-[4-(4-methoxybenzoyl)piperazino]ethyl]]-2,3,4,4a,5,9b-hexahydro-4a,9b-trans-1H-pyrido[4,3-b]indole;

(±)-8-fluoro-5-(4-fluorophenyl)-2-[2-(4-phenylacetyl-piperazino)ethyl]-2,3,4,4a,5,9b-hexahydro-4a,9b-trans-1H-pyrido[4,3-b]indole;

(±)-8-fluoro-5-(4-fluorophenyl)-2-[[2-[4-(3-chlorophenylacetyl)piperazino]ethyl]]-2,3,4,4a,5,9b-hexahydro-4a,9b-trans-1H-pyrido[4,3-b]indole;

(±)-8-fluoro-5-(4-fluorophenyl)-2-[3-(4-acetyl-piperazino)-1-propyl]-2,3,4,4a,5,9b-hexahydro-4a,9b-trans-1H-pyrido[4,3-b]indole;

(±)-8-fluoro-5-(4-fluorophenyl)-2-[4-(4-acetyl-piperazino)-1-butyl]-2,3,4,4a,5,9b-hexahydro-4a,9b-trans-1H-pyrido[4,3-b]indole;

(±)-8-fluoro-5-(4-fluorophenyl)-2-[5-(4-acetyl-piperazino)-1-pentyl]-2,3,4,4a,5,9b-hexahydro-4a,9b-trans-1H-pyrido[4,3-b]indole;

(±)-8-fluoro-5-(4-fluorophenyl)-2-[6-(4-acetyl-piperazino)-1-hexyl]-2,3,4,4a,5,9b-hexahydro-4a,9b-trans-1H-pyrido[4,3-b]indole;

(±)-8-fluoro-5-(4-fluorophenyl)-2-[2-(4-methanesulfonylpiperazino)ethyl]-2,3,4,4a,5,9b-hexahydro-4a,9b-trans-1H-pyrido[4,3-b]indole;

(±)-8-fluoro-5-(4-fluorophenyl)-2-[2-(4-benzenesulfonylpiperazino)ethyl]-2,3,4,4a,5,9b-hexahydro-4a,9b-trans-1H-pyrido[4,3-b]indole;

(±)-8-fluoro-5-(4-fluorophenyl)-2-[[2-[4(p-toluenesulfonyl)piperazino)ethyl]]-2,3,4,4a,5,9b-hexahydro-4a,9b-trans-1H-pyrido[4,3-b]indole; and (±)-8-fluoro-5-(4-fluorophenyl)-2-[[2-[4(4-chlorobenzenesulfonyl)piperazino]ethyl]]-2,3,4,4a,5,9b-hexahydro-4a,9b-trans-1H-pyrido[4,3-b]indole.

The same process, substituting the appropriate phenylpyridoindole for the difluorophenylpyridoindole, is used to prepare:

(+)-5-phenyl-2[2-(4-acetylpiperazino)ethyl]-2,3,4,4a,5,9b-hexahydro-4a,9b-trans-1H-pyrido[4,3-b]indole;

(±)-8-chloro-5-(4-chlorophenyl)-2-[2-(4-acetyl-piperazino)ethyl]-2,3,4,4a,5,9b-hexahydro-4a,9b-trans-1H-pyrido[4,3-b]indole;

(±)-8-fluoro-5-(3-methoxyphenyl)-2-[2-(4-acetyl-piperazino)ethyl]-2,3,4,4a,5,9b-hexahydro-4a,9b-trans-1H-pyrido[4,3-b]indole; and (±)-8-methyl-5-(3,4-dimethylphenyl)-2-[2-(4-acetyl-piperazino)ethyl]-2,3,4,4a,5,9b-hexahydro-4a,9b-trans-1H-pyrido[4,3-b]indole.

EXAMPLE 26

(+)-8-Fluoro-5-(4-fluorophenyl)-2-[2-(4-acetyl-piperazino)ethyl]-2,3,4,4a,5,9b-hexahydro-4a,9b-trans-1H-pyrido[4,3-b]indole Bis-hydrogen Maleate (+)-8-Fluoro-5-(4-fluorophenyl)-2,3,4,4a,5,9b-hexahydro-4a,9b-trans-pyrido[4,3-b]indole hydrochloride (526 mg, 1.63 mmole) was converted to free base according to the method of Example 3 and combined with 2-(4-acetylpiperazino)ethyl chloride (407 mg, 1.80 mmole) and triethylamine (0.50 ml, 3.6 mmole) in 40 ml of absolute ethanol. Following 3 hours of reflux, the title product was recovered, purified, converted to the salt form and recrystallized according to the procedure of the preceding Example. Yield: 340 mg [m.p. 195°–196° C., $[\alpha]_D^{25} = +10.6$ (c=0.5, methanol), m/e 440].

Analysis: Calcd. for $C_{25}H_{30}N_4OF_2\cdot 2C_4H_4O_4$: C, 58.92; H, 5.69; N, 8.33. Found: C, 58.47; H, 5.44; N, 8.20.

EXAMPLE 27

1-Benzyl-4-(4-chlorobutyryl)piperazine

N-Benzylpiperazine (1.0 g, 5.7 mmole) and triethylamine (1.17 ml, 8.5 mmole) were combined in 20 ml of methylene chloride. 4-Chlorovaleryl chloride (0.945 ml, 8.5 mmole) in 10 ml of methylene chloride was added dropwise over 20 minutes and the reaction mixture stirred for 16 hours at room temperature. Water (20 ml) was then added and the organic layer dried (anhydrous magnesium sulfate) and evaporated in vacuo to a gum. The gum was chromatographed on silica gel with ethyl acetate as eluant and tlc monitoring. Clean product fractions were combined and evaporated to yield the title product as a gum [920 mg, Rf 0.5 (ethyl acetate)].

Triethylamine is not essential to this acylation. If omitted, excess base is added to the aqueous quench.

In like manner, substituting the appropriate chloroacyl chloride for 4-chlorobutyryl chloride, the following compounds are prepared:

1-benzyl-4-(2-chloroacetyl)piperazine;
1-benzyl-4-(3-chloropropionyl)piperazine;
1-benzyl-4-(5-chlorovaleryl)piperazine; and
1-benzyl-4-(6-chlorohexanoyl)piperazine.

In like manner, substituting the appropriate N-substituted piperazine for 1-benzylpiperazine, the following compounds are prepared:

1-(4-chlorobutyryl)-4-phenylpiperazine;
1-(4-chlorobutyryl)-4-methylpiperazine;
1-(4-chlorobutyryl)-4-isopropylpiperazine;
1-(4-chlorobutyryl)-4-(4-methylphenyl)piperazine;
1-acetyl-4-(4-chlorobutyryl)piperazine;
1-(4-chlorobutyryl)4-(4-methoxybenzoyl)piperazine;
1-(3-bromobenzoyl)-4-(4-chlorobutyryl)piperazine;
1-(4-chlorobutyryl)-4-(2-fluorobenzoyl)piperazine; and
1-(4-chlorobutyryl)-4-(3-chloro-4-ethylbenzoyl)piperazine.

EXAMPLE 28

(±)-8-Fluoro-5-(4-fluorophenyl)-2-[3-(4-benzyl-piperazinocarbonyl)-1-propyl]-2,3,4,4a,5,9b-hexahydro-4a,9b-trans-1H-pyrido[4,3-b]indole Bis-hydrochloride By the methods of Example 2, (±)-8-fluoro-5-(4-fluorophenyl)-2,3,4,4a,5,9b-hexahydro-4a,9b-trans-1H-pyrido[4,3-b]indole (625 mg, 2.2 mmole) was reacted with 1-benzyl-4-(4-chlorobutyryl)piperazine to yield chromatographed free base form of the title product. The base was taken into acetone, converted to the bis-hydrochloride with excess ethereal hydrogen chloride, and the title product isolated by evaporation to dryness and repulp in ether [0.485 g, m/e 530].

Analysis: Calcd. for $C_{32}H_{36}ON_4F_2 \cdot 2HCl \cdot 2.25H_2O$: C, 59.67; H, 6.52; N, 8.69. Found: C, 59.55; H, 6.53; N, 8.68.

In like manner, substituting an equivalent amount of the appropriate organic chloride of the preceding Example for the chlorobutyrylpiperazine, the following compounds are prepared:

(±)-8-fluoro-5-(4-fluorophenyl)-2-[1-(4-benzyl-piperazinocarbonyl)methyl]-2,3,4,4a,5,9b-hexahydro-4a,9b-trans-1H-pyrido[4,3-b]indole;

(±)-8-fluoro-5-(4-fluorophenyl)-2-[2-(4-benzyl-piperazinocarbonyl)ethyl]-2,3,4,4a,5,9b-hexahydro-4a,9b-trans-1H-pyrido[4,3-b]indole;

(±)-8-fluoro-5-(4-fluorophenyl)-2-[4-benzyl-piperazinocarbonyl)butyl]-2,3,4,4a,5,9b-hexahydro-4a,9b-trans-1H-pyrido[4,3-b]indole;

(±)-8-fluoro-5-(4-fluorophenyl)-2-[5-(4-benzyl-piperazinocarbonyl)pentyl]-2,3,4,4a,5,9b-hexahydro-4a,9b-trans-1H-pyrido[4,3-b]indole;

(±)-8-fluoro-5-(4-fluorophenyl)-2-[3-(4-phenyl-piperazinocarbonyl)-1-propyl]-2,3,4,4a,5,9b-hexahydro-4a,9b-trans-1H-pyrido[4,3-b]indole;

(±)-8-fluoro-5-(4-fluorophenyl)-2-[3-(4-methyl-piperazinocarbonyl)-1-propyl]-2,3,4,4a,5,9b-hexahydro-4a,9b-trans-1H-pyrido[4,3-b]indole;

(±)-8-fluoro-5-(4-fluorophenyl)-2-[3-(4-isopropyl-piperazinocarbonyl)-1-propyl]-2,3,4,4a,5,9b-hexahydro-4a,9b-trans-1H-pyrido[4,3-b]indole;

(±)-8-fluoro-5-(4-fluorophenyl)-2-[[3-[4-(4-methyl-phenyl)piperazinocarbonyl]-1-propyl]]-2,3,4,4a,5,9b-hexahydro-4a,9b-trans-1H-pyrido[4,3-b]indole;

(±)-8-fluoro-5-(4-fluorophenyl)-2-[3-(4-acetyl-piperazinocarbonyl)-1-propyl]-2,3,4,4a,5,9b-hexahydro-4a,9b-trans-1H-pyrido[4,3-b]indole;

(±)-8-fluoro-5-(4-fluorophenyl)-2-[[3-[4-(4-methoxybenzoyl)piperazinocarbonyl]-1-propyl]]-2,3,4,4a,5,9b-hexahydro-4a,9b-trans-1H-pyrido[4,3-b]indole;

(±)-8-fluoro-5-(4-fluorophenyl)-2-[[3-[4-(3-bromobenzoyl)piperazinocarbonyl]-1-propyl]]-2,3,4,4a,5,9b-hexahydro-4a,9b-trans-1H-pyrido[4,3-b]indole;

(±)-8-fluoro-5-(4-fluorophenyl)-2-[[3-[4-(2-fluorobenzoyl)piperazinocarbonyl]-1-propyl]]-2,3,4,4a,5,9b-hexahydro-4a,9b-trans-1H-pyrido[4,3-b]indole; and (±)-8-fluoro-5-(4-fluorophenyl)-2-[[3-[4-(3-chloro-2-ethylbenzoyl)piperazinocarbonyl]-1-propyl]]-2,3,4,4a,5,9b-hexahydro-4a,9b-trans-1H-pyrido[4,3-b]indole.

EXAMPLE 29

(±)-8-Fluoro-5-(4-fluorophenyl)-2-[4-(4-benzyl-piperazino)-1-butyl)]-2,3,4,4a,5,9b-hexahydro-4a,9b-trans-1H-pyrido[4,3-b]indole Tris-hydrochloride (±)-8-Fluoro-5-(4-fluorophenyl)-2-[3-(4-benzyl-piperazinocarbonyl)-1-propyl]-2,3,4,4a,5,9b-hexahydro-4a,9b-trans-1H-pyrido[4,3-b]indole bis-hydrochloride (1 g) was taken into 30 ml of tetrahydrofuran. Lithium aluminum hydride (about 9 equivalents) was added portionwise; evolution of hydrogen was noted during most of the addition. After stirring for an additional 30 minutes at room temperature, an excess of Glauber's salt (sodium sulfate decahydrate) was added and the mixture stirred for an additional 10 minutes. The reaction mixture was filtered with tetrahydrofuran wash and the combined filtrate and washes evaporated to dryness. The resulting gum was taken up in acetone and converted to the hydrochloride salt by the addition of ethereal hydrogen chloride. The resulting slurry was taken to dryness, repulped in a mixture of 30 ml of acetone and 10 ml of methanol, and filtered to yield the title product [120 mg, Rf 0.2 (methanol); m/e 516].

Analysis: Calcd. for $C_{32}H_{38}N_4F_2 \cdot 3HCl$ C, 61.39; H, 6.59; N, 8.95. Found: C, 61.26; H, 6.68; N, 8.78.

In like manner, employing sufficient lithium aluminum hydride to react with acid protons, if present, and one or two amide functions as present, the other amides and bis-amides of the preceding Example are reduced to:

(±)-8-fluoro-5-(4-fluorophenyl)-2-[2-(4-benzyl-piperazino)ethyl]-2,3,4,4a,5,9b-hexahydro-4a,9b-trans-1H-pyrido[4,3-b]indole;

(±)-8-fluoro-5-(4-fluorophenyl)-2-[3-(4-benzyl-piperazino)-1-propyl]-2,3,4,4a,5,9b-hexahydro-4a,9b-trans-1H-pyrido[4,3-b]indole;

(±)-8-fluoro-5-(4-fluorophenyl)-2-[5-(4-benzyl-piperazino)-1-pentyl]-2,3,4,4a,5,9b-hexahydro-4a,9b-trans-1H-pyrido[4,3-b]indole;

(±)-8-fluoro-5-(4-fluorophenyl)-2-[6-(4-benzyl-piperazino)-1-hexyl]-2,3,4,4a,5,9b-hexahydro-4a,9b-trans-1H-pyrido[4,3-b]indole;

(±)-8-fluoro-5-(4-fluorophenyl)-2-[4-(4-phenyl-piperazino)-1-butyl]-2,3,4,4a,5,9b-hexahydro-4a,9b-trans-1H-pyrido[4,3-b]indole;

(±)-8-fluoro-5-(4-fluorophenyl)-2-[4-(4-methyl-piperazino)-1-butyl]-2,3,4,4a,5,9b-hexahydro-4a,9b-trans-1H-pyrido[4,3-b]indole;

(±)-8-fluoro-5-(4-fluorophenyl)-2-[4-(4-isopropyl-piperazino)-1-butyl]-2,3,4,4a,5,9b-hexahydro-4a,9b-trans-1H-pyrido[4,3-b]indole;

(±)-8-fluoro-5-(4-fluorophenyl)-2-[4-(4-ethyl-piperazino)-1-butyl]-2,3,4,4a,5,9b-hexahydro-4a,9b-trans-1H-pyrido[4,3-b]indole;

(±)-8-fluoro-5-(4-fluorophenyl)-2-[[4-[4-(4-methoxybenzyl)piperazino]-1-butyl]]-2,3,4,4a,5,9b-hexahydro-4a,9b-trans-1H-pyrido[4,3-b]indole;

(±)-8-fluoro-5-(4-fluorophenyl)-2-[[4-[4-(3-bromobenzyl)piperazino]-1-butyl]]-2,3,4,4a,5,9b-hexahydro-4a,9b-trans-1H-pyrido[4,3-b]indole;

(±)-8-fluoro-5-(4-fluorophenyl)-2-[[4-[4-(2-fluorobenzyl)piperazino]-1-butyl]]-2,3,4,4a,5,9b-hexahydro-4a,9b-trans-1H-pyrido[4,3-b]indole; and (±)-8-fluoro-5-(4-fluorophenyl)-2-[[4-[4-(3-chloro-2-ethylbenzyl)piperazino]-1-butyl]]-2,3,4,4a,5,9b-hexahydro-4,a,9b-trans-1H-pyrido[4,3-b]indole.

EXAMPLE 30

(±)-8-Fluoro-5-(4-fluorophenyl)-2-(4-piperazino-1-butyl)-2,3,4,4a,5,9b-hexahydro-4a,9b-trans-1H-pyrido[4,3-b]indole Tris-hydrochloride The entire batch of (±)-8-fluoro-5-(4-fluorophenyl)-2-[4-(4-benzylpiperazino)-1-butyl]-2,3,4,4a,5,9b-hexahydro-4a,9b-trans-1H-pyrido[4,3-b]-indole tris-hydrochloride from the preceding Example was taken into 10 ml of ethanol containing 3 drops of concentrated hydrochloric acid. Hydrogenation catalyst (10% Pd/C, 250 mg) was added and the mixture hydrogenated for 6 hours at 50 psi and 40° C. The catalyst was recovered by filtration with ethanol wash. The combined filtrate and washes were evaporated to a gum. The gum dissolved in the minimum methanol and was crystallized by adding 100 ml of acetone and stirring for 30 minutes. The yield of title product as a trihydrate was 0.3 g (m.p. 229°-232° C.).

In the same manner, the other benzyl derivatives of the preceding Example are hydrogenolyzed to:

(±)-8-fluoro-5-(4-fluorophenyl)-2-(2-piperazinoethyl)-2,3,4,4a,5,9b-hexahydro-4a,9b-trans-1H-pyrido[4,3-b]indole;

(±)-8-fluoro-5-(4-fluorophenyl)-2-(3-piperazino-1-propyl)-2,3,4,4a,5,9b-hexahydro-4a,9b-trans-1H-pyrido[4,3-b]indole;

(±)-8-fluoro-5-(4-fluorophenyl)-2-(5-piperazino-1-pentyl)-2,3,4,4a,5,9b-hexahydro-4a,9b-trans-1H-pyrido[4,3-b]indole; and (±)-8-fluoro-5-(4-fluorophenyl)-2-(6-piperazino-1-hexyl)-2,3,4,4a,5,9b-hexahydro-4a,9b-trans-1H-pyrido[4,3-b]indole.

EXAMPLE 31

(±)-8-Fluoro-5-(4-fluorophenyl)-2-[4-(4-acetylpiperazino)-1-butyl]-2,3,4,4a,5,9b-hexahydro-4a,9b-trans-1H-pyrido[4,3-b]indole Bis-hydrochloride.

(±)-8-Fluoro-5-(4-fluorophenyl)-2-(4-piperazino-1-butyl)-2,3,4,4a,5,9b-hexahydro-4a,9b-trans-1H-pyrido[4,3-b]indole tris-hydrochloride trihydrate (377 mg, 0.64 mmole) and triethylamine (0.68 ml, 4.92 mmole) were taken up in 8 ml of methylene chloride. Acetyl chloride (0.055 ml, 0.77 mmole) in 4 ml of methylene chloride was added dropwise over 20 minutes and the mixture stirred overnight at room temperature. Water (12 ml) was then added to the reaction mixture. The organic layer was dried over anhydrous magnesium sulfate filtered and evaporated to a gum. The gum was taken up in ether, converted to hydrochloride salt by the addition of ethereal hydrogen chloride, the mixture evaporated to dryness and the residue repulped in acetone, from which the title product was obtained as a hygroscopic solid (150 mg).

Analysis: Calcd. for $C_{27}H_{34}N_4OF_2.2HCl.2H_2O$: C, 56.15; H, 6.92; N, 9.69. Found: C, 56.31; H, 7.24; N, 9.75.

In like manner, the other piperazine derivatives of the preceding Example are acetylated to yield:

(±)-8-fluoro-5-(4-fluorophenyl)-2-[2-(4-acetylpiperazino)ethyl]-2,3,4,4a,5,9b-hexahydro-4a,9b-trans-1H-pyrido[4,3-b]indole;

(±)-8-fluoro-5-(4-fluorophenyl)-2-[3-(4-acetylpiperazino)-1-propyl]-2,3,4,4a,5,9b-hexahydro-4a,9b-trans-1H-pyrido[4,3-b]indole;

(±)-8-fluoro-5-(4-fluorophenyl)-2-[5-(4-acetylpiperazino)-1-pentyl]-2,3,4,4a,5,9b-hexahydro-4a,9b-trans-1H-pyrido[4,3-b]indole; and (±)-8-fluoro-5-(4-fluorophenyl)-2-[6-(4-acetylpiperazino)-1-hexyl]-2,3,4,4a,5,9b-hexahydro-4a,9b-trans-1H-pyrido[4,3-b]indole.

Substitution of acetyl chloride with the appropriate acyl chloride, alkyl chloroformate or sulfonyl chloride in this process is used to produce:

(±)-8-fluoro-5-(4-fluorophenyl)-2-[2-(4-propionylpiperazino)ethyl]-2,3,4,4a,5,9b-hexahydro-4a,9b-trans-1H-pyrido[4,3-b]indole;

(±)-8-fluoro-5-(4-fluorophenyl)-2-[2-(4-isovalerylpiperazino)ethyl]-2,3,4,4a,5,9b-hexahydro-4a,9b-trans-1H-pyrido[4,3-b]indole;

(±)-8-fluoro-5-(4-fluorophenyl)-2-[2-(4-benzoylpiperazino)ethyl]-2,3,4,4a,5,9b-hexahydro-4a,9b-trans-1H-pyrido[4,3-b]indole;

(±)-8-fluoro-5-(4-fluorophenyl)-2-[[2-[4-(4-methoxybenzoyl)piperazino]ethyl]]-2,3,4,4a,5,9b-hexahydro-4a,9b-trans-1H-pyrido[4,3-b]indole;

(±)-8-fluoro-5-(4-fluorophenyl)-2-[[2-[4-(4-ethylbenzoyl)piperazino]ethyl]]-2,3,4,4a,5,9b-hexahydrol-4a,9b-trans-1H-pyrido[4,3-b]indole;

(±)-8-fluoro-5-(4-fluorophenyl)-2-[2-(4-phenylacetylpiperazino)ethyl]-2,3,4,4a,5,9b-hexahydro-4a,9b-trans-1H-pyrido[4,3-b]indole;

(±)-8-fluoro-5-(4-fluorophenyl)-2-[2-(4-ethoxycarbonylpiperazino)ethyl]-2,3,4,4a,5,9b-hexahydro-4a,9b-trans-1H-pyrido[4,3-b]indole;

(±)-8-fluoro-5-(4-fluorophenyl)-2-[2-(4-methanesulfonylpiperazino)ethyl]-2,3,4,4a,5,9b-hexahydro-4a,9b-trans-1H-pyrido[4,3-b]indole;

(±)-8-fluoro-5-(4-fluorophenyl)-2-[[2-[4-(3-methylphenyl)sulfonylpiperazino]ethyl]]-2,3,4,4a,5,9b-hexahydro-4a,9b-trans-1H-pyrido[4,3-b]indole.

Anhydrides can be substituted for acyl chlorides in the process. Acetoformic acid reagent [cf Blackwood et al, J. Am. Chem. Soc. 82, pp. 5194–5197 (1960)] is substituted for acetyl chloride to produce:

(±)-8-fluoro-5-(4-fluorophenyl)-2-[2-(4-formylpiperazino)ethyl]-2,3,4,4a,5,9b-hexahydro-4a,9b-trans-1H-pyrido[4,3-b]indole.

EXAMPLE 32

(±)-8-Fluoro-5-(4-fluorophenyl)-2-(3-piperazinocarbonyl-1-propyl)-2,3,4,4a,5,9b-hexahydro-4a,9b-trans-1H-pyrido[4,3-b]indole Bis-hydrochloride (±)-8-Fluoro-5-(4-fluorophenyl)-2-[3-(4-benzylpiperazinocarbonyl)-1-propyl]-2,3,4,4a,5,9b-hexahydro-4a,9b-trans-1H-pyrido[4,3-b]indole bis-hydrochoride from Example 28 (1 g) was hydrogenated in 20 ml of ethanol containing 6 drops of concentrated hydrochloric acid in the presence of 300 mg of 10% Pd/C catalyst at 45 psi and 40° C. for 16 hours. The catalyst was recovered by filtration and the mother liquor evaporatd to a gum. The gum was crystallized by slurry with acetone [0.640 g; ir (KBr) 1470, 1508, 1639, 1733, 3390 $Cm^{-1}$; m/e 440].

Analysis: Calcd. for $C_{25}H_{30}N_4OF_2.2HCl.3H_2O$: C, 52.91; H, 6.69; N, 9.87. Found: C, 52.61; H, 6.53; N, 9.93.

EXAMPLE 33

(±)-8-Fluoro-5-(4-fluorophenyl)-2-(4-piperazino-1-butyl)-2,3,4,4a,5,9b-hexahydro-4a,9b-trans-1H-pyrido[4,3-b]indole By the method of Example 29 employing about 10.5 equivalents of lithium aluminum hydride, the piperazinocarbonyl compound of the preceding Example is reduced to the title product. The crude is converted to tris-hydrochloride and purified according to Example 30.

EXAMPLE 34

(±)-8-Fluoro-5-(4-fluorophenyl)-2-[3-(4-acetyl-piperazinocarbonyl)-1-propyl]-2,3,4,4a,5,9b-hexahydro-4a,9b-trans-1H-pyrido[4,3-b]indole Hydrochloride The piperazinocarbonyl compound of the twice preceding Example (500 mg, 1.14 mmole), acetyl chloride (0.089 ml, 1.25 mmole) and triethylamine (0.628 ml, 4.5 mmole) in a total of 15 ml of methylene chloride were reacted by the methods of Example 31. The crude product (isolated from the methylene chloride after aqueous quench) was chromatographed on silica gel with 1:1 methanol:ethyl acetate as eluant and tlc monitoring [Rf 0.2 (1:1 methanol:ethyl acetate)]. Clean product containing fractions were combined and evaporated to dryness. The resulting gum was taken up in ether, converted to hydrochloride by the addition of ethereal hydrogen chloride and evaporated to solids. Repulp of the solids in 10 ml of acetone and filtration gave the title product (50 mg, m.p. 220°–223° C.).

Analysis: Calcd. for $C_{27}H_{32}N_4O_2F\cdot HCl\cdot 0.75\ H_2O$: C, 60.90; H, 6.54; N, 10.52. Found: C, 60.96; H, 6.44; N, 10.32.

The product of this Example is reduced with hydride to yield (±)-8-fluoro-5-(4-fluorophenyl)-2-[4-(3-ethyl-piperazino)-1-butyl]-2,3,4,4a,5,9b-hexahydro-4a,9b-trans-1H-pyrido[4,3-b]indole according to Example 29 above.

EXAMPLE 35

(±)-8-Fluoro-5-(4-fluorophenyl)-2-[4-(4-acetyl-piperazino)-1-butyl]-2,3,4,4a,5,9b-hexahydro-4a,9b-trans-1H-pyrido-[4,3-b]indole Bis-hydrochloride (±)-8-Fluoro-5-(4-fluorophenyl)-2-(4-bromo-1-butyl)-2,3,4,4a,5,9b-hexahydro-4a,9b-trans-1H-pyrido[4,3-b]indole of Example 8 is reacted with 5 equivalents of 1-acetylpiperazine in refluxing ethanol according to Example 25. The reaction mixture is evaporated to dryness to yield the hydrobromide salt. The latter is partitioned between aqueous sodium hydroxide and ether; the aqueous layer is further extracted with ether. The combined ether layer and extracts are dried, evaporated to dryness and converted to title product according to Example 31.

By the same procedure, substituting 1-acetylpiperazine with 10 equivalents of piperazine, (±)-8-fluoro-5-(4-fluorophenyl)-2-(4-piperazino-1-butyl)-2,3,4,4a,5,9b-hexahydro-4a,9b-trans-1H-pyrido[4,3-b]indole is prepared by the same method.

Alternatively, the intermediate acyl derivative of Example 8 reacted with excess piperazine to yield (±)-8-fluoro-5-(4-fluorophenyl)-2-(3-piperazinocarbo-nyl-1-propyl)-2,3,4,4a,5,9b-hexahydro-4a,9b-trans-1H-pyrido[4,3-b]indole. The latter is reduced with lithium aluminum hydride according to Example 29 and then acylated to yield the title product.

EXAMPLE 36

(±)-8-Fluoro-5-(4-fluorophenyl)-2-[4-(4-acetyl-piperazino)-1-butyl]-2,3,4,4a,5,9b-hexahydro-4a,9b-trans-1H-pyrido[4,3-b]indole (±)-8-Fluoro-5-(4-fluorophenyl)-2-(4-amino-1-butyl)-2,3,4,4a,5,9b-hexahydro-4a,9b-trans-1H-pyrido[4,3-b]indole hydrochloride of Example 11 is converted to free base form in 3-methyl-2-pentanone by partitioning between excess dilute sodium hydroxide and the ketone solvent. The organic layer is separated, dried over anhydrous magnesium sulfate and filtered. An equimolar portion of N,N-bis(2-chloroethyl)acetamide (derived from diethylamine by N-acetylation and conversion to the bis-chloride) and excess sodium carbonate are added to filtrate, and the mixture heated at 85° C. for 16 hours. Evaporation to dryness yields the title product as bis-hydrochloride.

EXAMPLE 37

1-(4-Chloro-1-butyl)-2,3-indolinedione

Sodium hydride (50% dispersion in oil, 1.63 g, 34 mmole) under dry nitrogen was washed with 50 ml of ether to remove the oil. The ether was separated by decantation. Dimethylformamide (25 ml) was added to the ether wet sodium hydride. A solution of 2,3-indolinedione (isatin, 5 g, 34 mmole) and 1,4-dichlorobutane (21.6 g, 18.6 ml, 0.17 mmole) in 200 ml of dimethylformamide was added dropwise over 1 hour, maintaining the temperature at 25°–28° C. The resulting solution was stirred for 1 hour at room temperature. The reaction mixture was filtered, and the filtrate evaporated to 30 ml and diluted with 50 ml of methylene chloride. The resulting mixture was again filtered, the filtrate evaporated to dryness and the residue slurried in 200 ml of ether. The ether was decanted from a drum and evaporated to yield the title product [830 mg, Rf 0.55 1:1 ethyl acetate:hexane)].

By the same method 2-pyrroline-4,5-dione, 2,3-pyrrolidinedione and 2,3-piperidinedione are converted, respectively, to 1-(4-chloro-1-butyl)-2-pyrroline-4,5-dione, 1-(4-chloro-1-butyl)-2,3-pyrrolidinedione and 1-(4-chloro-1-butyl)-2,3-piperidinedione.

EXAMPLE 38

(±)-8-Fluoro-5-(4-fluorophenyl)-2-[4-(2,3-indoline-dion-1-yl)-1-butyl]-2,3,4,4a,5,9b-hexahydro-4a,9b-trans-1H-pyrido[4,3-b]indole Hydrochloride 1-(4-Chloro-1-butyl)-2,3-indolinedione (830 mg, 3.5 mmole), (±)-8-fluoro-5-(4-fluorophenyl)-2-2,3,4,4a,5,9b-hexahydro-4a,9b-trans-1H-pyrido[4,3-b]indole (500 mg, 1.75 mmole), anhydrous sodium carbonate (1.1 g, 10.4 mmole) and potassium iodide (5 mg) were combined in 3-methyl-2-butanone (20 ml) and refluxed for 16 hours. The reaction mixture was evaporated to dryness and the residue partitioned between 50 ml of methylene chloride and 50 ml of water. The aqueous phase was washed with 50 ml additional methylene chloride. The organic layers were combined, dried over anhydrous magnesium sulfate, filtered and evaporated to a gum. The gum was chromatographed on silica gel using ethyl acetate and monitoring by tlc. Clean product containing fractions were combined and evaporated to dryness. The residue was triturated with ethereal hydrogen chloride to yield the title product [226 mg; ir (KBr) 1477, 1520, 1623, 1724, 3390 $cm^{-1}$].

By the same method, the other 4-chloro-1-butyl compounds of the preceding Example are converted to:
(±)-8-fluoro-5-(4-fluorophenyl)-2-[4-(2-pyrroline-4,5-dion-1-yl)-1-butyl]-2,3,4,4a,5,9b-hexahydro-4a,9b-trans-1H-pyrido[4,3-b]indole;
(±)-8-fluoro-5-(4-fluorophenyl)-2-[4-(piperidine-2,3-dion-1-yl)-1-butyl]-2,3,4,4a,5,9b-hexahydro-4a,9b-trans-1H-pyrido[4,3-b]indole; and (±)-8-fluoro-5-(4-fluorophenyl)-2-[4-(piperidine-2,3-dion-1-yl)-1-butyl]-2,3,4,4a,5,9b-hexahydro-4a,9b-trans-1H-pyrido[4,3-b]indole.

By the same method, substituting the appropriately substituted pyrido[4,3-b]indole for the difluoropyrido[4,3-b]indole, the following compounds are prepared:

(+)-8-fluoro-5-(4-fluorophenyl)-2-[4-(indoline-2,3-dion-1-yl)-1-butyl]-2,3,4,4a,5,9b-hexahydro-4a,9b-trans-1H-pyrido[4,3-b]indole;

(±)-8-fluoro-5-(3,4-difluorophenyl)-2-[4-(indoline-2,3-dion-1-yl)-1-butyl]-2,3,4,4a,5,9b-hexahydro-4a,9b-trans-1H-pyrido[4,3-b]indole;

(±)-8-chloro-5-phenyl-2-[4-(indoline-2,3-dion-1-yl)-1-butyl]-2,3,4,4a,5,9b-hexahydro-4a,9b-trans-1H-pyrido[4,3-b]indole; and (±)-8-methyl-5-(4-methylphenyl)-2-[4-(indoline-2,3-dion-1-yl)-1-butyl]-2,3,4,4a,5,9b-hexahydro-4a,9b-trans-1H-pyrido[4,3-b]indole

EXAMPLE 39

(±)-8-Fluoro-5-(4-fluorophenyl)-2-[4-(1,3-dioxolan-2-yl)-1-butyl]-2,3,4,4a,5,9b-hexahydro-4a,9b-trans-1H-pyrido[4,3-b]indole By the procedure of Example 37, (±)-8-fluoro-5-(4-fluorophenyl)-2-2,3,4,4a,5,9b-hexahydro-4a,9b-trans-1H-pyrido[4,3-b]indole is reacted with 2-(4-chloro-1-butyl)-2,3-dioxolane (the ethyleneglycol acetal of 5-chlorovaleraldehyde) to yield the title product.

By the same method, 2-(2-bromo-1-ethyl)-2,3-dioxolane, 2-(3-mesyloxy-1-propyl)-2,3-dioxolane and 2-(5-iodo-1-pentyl)-2,3-dioxolane are reacted to produce, respectively:

(±)-8-fluoro-5-(4-fluorophenyl)-2-[2-(1,3-dioxalan-2-yl)-1-ethyl]-2,3,4,4a,5,9b-hexahydro-4a,9b-trans-1H-pyrido[4,3-b]indole;

(±)-8-fluoro-5-(4-fluorophenyl)-2-[3-(1,3-dioxolan-2-yl)-1-propyl]-2,3,4,4a,5,9b-hexahydro-4a,9b-trans-1H-pyrido[4,3-b]indole; and (±)-8-fluoro-5-(4-fluorophenyl)-2-[5-(1,3-dioxolan-2-yl)-1-pentyl]-2,3,4,4a,5,9b-hexahydro-4a,9b-trans-1H-pyrido[4,3-b]indole.

EXAMPLE 40

(±)-8-Fluoro-5-(4-fluorophenyl)-2-(5-oxo-1-pentyl)-2,3,4,4a,5,9b-hexahydro-4a,9b-trans-1H-pyrido[4,3-b]indole Acetal from the preceding Example (1 g) is heated to 40°–45° C. in a mixture of 10 ml of 1 N hydrochloric acid and 10 ml of water for 4 hours. The methanol is removed in vacuo and the aqueous residue made basic with 5% sodium bicarbonate. The mixture is extracted with two 15 ml portions of methylene chloride. The organic extracts are combined, dried over anhydrous sodium sulfate, filtered and evaporated to yield the title product. Alternatively, dilute acid is introduced into the work-up stage of the preceding Example, and the title product isolated directly without isolation of the intermediate acetal.

By the same method, the other acetals of the preceding Example ae converted to:

(±)-8-fluoro-5-(4-fluorophenyl)-2-(3-oxo-1-propyl)-2,3,4,4a,5,9b-hexahydro-4a,9b-trans-1H-pyrido[4,3-b]indole;

(±)-8-fluoro-5-(4-fluorophenyl)-2-(4-oxo-1-butyl)-2,3,4,4a,5,9b-hexahydro-4a,9b-trans-1H-pyrido[4,3-b]indole; and (±)-8-fluoro-5-(4-fluorophenyl)-2-(6-oxo-1-hexyl)-2,3,4,4a,5,9b-hexahydro-4a,9b-trans-1H-pyrido[4,3-b]indole.

EXAMPLE 41

(±)-8-Fluoro-5-(4-fluorophenyl)-2-(5-hydroxyimino-1-pentyl)-2,3,4,4a,5,9b-hexahydro-4a,9b-trans-1H-pyrido[4,3-b]indole Aminoaldehyde from the preceding Example (370 mg, 1 mmole) is dissolved in 5 ml of ethanol. Hydroxylamine hydrochloride (69.5 mg, 1 mmole) and sodium bicarbonate (84 mg, 1 mmole) are added and the mixture refluxed for 16 hours. The reaction mixture is evaporated to dryness and the residue partitioned between methylene chloride and water. The organic phase is dried and evaporated to yield the title product.

By the same method the other aldehydes of Example 41 are converted to:

(±)-8-fluoro-5-(4-fluorophenyl)-2-(3-hydroxyimino-1-propyl)-2,3,4,4a,5,9b-hexahydro-4a,9b-trans-1H-pyrido[4,3-b]indole;

(±)-8-fluoro-5-(4-fluorophenyl)-2-(4-hydroxyimino-1-butyl)-2,3,4,4a,5,9b-hexahydro-4a,9b-trans-1H-pyrido[4,3-b]indole; and (±)-8-fluoro-5-(4-fluorophenyl)-2-(6-hydroxyimino-1-hexyl)-2,3,4,4a,5,9b-hexahydro-4a,9b-trans-1H-pyrido[4,3-b]indole.

Substituting an equivalent of the appropriate substituted hydrazine hydrochloride for hydroxylamine hydrochloride (or substituted hydrazine base, omitting sodium bicarbonate) the following compounds are prepared:

(±)-8-fluoro-5-(4-fluorophenyl)-2-(5-methylhydrazono-1-pentyl)-2,3,4,4a,5,9b-hexahydro-4a,9b-trans-1H-pyrido[4,3-b]indole;

(±)-8-fluoro-5-(4-fluorophenyl)-2-(5-benzylhydrazono-1-pentyl)-2,3,4,4a,5,9b-hexahydro-4a,9b-trans-1H-pyrido[4,3-b]indole; and (±)-8-fluoro-5-(4-fluorophenyl)-2-(5-acetylhydrazono-1-pentyl)-2,3,4,4a,5,9b-hexahydro-4a,9b-trans-1H-pyrido[4,3-b]indole.

EXAMPLE 42

(±)-8-Fluoro-5-(4-fluorophenyl)-2-(5-hydroxyamino-1-pentyl)-2,3,4,4a,5,9b-hexahydro-4a,9b-trans-1H-pyrido(4,3-b)indole Oxime from the preceding Example (385 mg, 1 mmole) is combined with 10% aqueous methanol and the pH adjusted to 2–3. Sodium cyanoborohydride (189 mg, 3 mmoles) is added, and the mixture stirred for 4 hours at room temperature, maintaining the the pH at 2–3 by addition of dilute mineral acid. The reaction mixture is then allowed to stir for an additional 16 hours at room temperature, made basic and extracted with methylene chloride. The extract is dried, filtered and evaporated to yield the title product.

By the same method, the other oximes and hydrazones of the preceding Example are converted to:

(±)-8-fluoro-5-(4-fluorophenyl)-2-(3-hydroxyamino-1-propyl)-2,3,4,4a,5,9b-hexahydro-4a,9b-trans-1H-pyrido[4,3-b]indole;

(±)-8-fluoro-5-(4-fluorophenyl)-2-(4-hydroxyamino-1-butyl)-2,3,4,4a,5,9b-hexahydro-4a,9b-trans-1H-pyrido[4,3-b]indole;

(±)-8-fluoro-5-(4-fluorophenyl)-2-(6-hydroxyamino-1-hexyl)-2,3,4,4a,5,9b-hexahydro-4a,9b-trans-1H-pyrido[4,3-b]indole;

(±)-8-fluoro-5-(4-fluorophenyl)-2-[5-(2-methylhydrazino)-1-pentyl]-2,3,4,4a,5,9b-hexahydro-4a,9b-trans-1H-pyrido[4,3-b]indole;
(±)-8-fluoro-5-(4-fluorophenyl)-2-[5-(2-benzylhydrazino)-1-pentyl]-2,3,4,4a,5,9b-hexahydro-4a,9b-trans-1H-pyrido[4,3-b]indole; and
(±)-8-fluoro-5-(4-fluorophenyl)-2-[5-(2-acetylhydrazino)-1-pentyl]-2,3,4,4a,5,9b-hexahydro-4a,9b-trans-1H-pyrido[4,3-b]indole.

EXAMPLE 43

(±)-8-Fluoro-5-(4-fluorophenyl-2-[5-(1,2,4-oxadiazolidine-3,5-dion-2-yl)-1-pentyl]-2,3,4,4a,5,9b-hexahydro-4a,9b-trans-1H-pyrido[4,3-b]indole Hydroxyamino compound of the preceding Example (387 mg, 1 mmole) is combined with 7.5 ml of chloroform and cooled to 0°–5° C. Triethylamine (222 mg, 2.2 mmole) is added followed by the dropwise addition of chlorocarbonyl isocyanate (116 mg, 1.1 mmole) in 3 ml of chloroform, keeping the temperature 0°–10° C. The reaction mixture is allowed to warm to room temperature, stirred for an additional 3 hours, and diluted with dilute aqueous sodium hydroxide. The organic layer is discarded and the aqueous layer adjusted to isoelectric pH to precipitate the title product. Alternatively, the aqueous layer is acidified with dilute hydrochloric acid and the title product extracted into 1-butanol as the hydrochloride salt. The latter is isolated by evaporating the dried butanol layer to dryness.

By the same method the other hydroxyamino and hydrazino compounds of the preceding Example are converted to:
(±)-8-fluoro-5-(4-fluorophenyl)-2-[3-(1,2,4-oxadiazolidine-3,5-dion-2-yl)-1-propyl]-2,3,4,4a,5,9b-hexahydro-4a,9b-trans-1H-pyrido[4,3-b]indole;
(±)-8-fluoro-5-(4-fluorophenyl)-2-[4-(1,2,4-oxadiazolidine-3,5-dion-1-yl)-1-butyl]-2,3,4,4a,5,9b-hexahydro-4a,9b-trans-1H-pyrido[4,3-b]indole;
(±)-8-fluoro-5-(4-fluorophenyl)-2-[6-(1,2,4-oxadiazolidine-3,5-dion-2-yl)-1-hexyl]-2,3,4,4a,5,9b-hexahydro-4a,9b-trans-1H-pyrido[4,3-b]indole;
(±)-8-fluoro-5-(4-fluorophenyl)-2-[5-(1-methyl-1,2,4-triazolidine-3,5-dion-2-yl)-1-pentyl]-2,3,4,4a,5,9b-hexahydro-4a,9b-trans-1H-pyrido[4,3-b]indole;
(±)-8-fluoro-5-(4-fluorophenyl)-2-[5-(1-benzyl-1,2,4-triazolidine-3,5-dion-2-yl)-1-pentyl]-2,3,4,4a,5,9b-hexahydro-4a,9b-trans-1H-pyrido[4,3-b]indole; and
(±)-8-fluoro-5-(4-fluorophenyl)-2-[5-(1-acetyl-1,2,4-triazolidine-3,5-dion-2-yl)-1-pentyl]-2,3,4,4a,5,9b-hexahydro-4a,9b-trans-1H-pyrido[4,3-b]indole.

EXAMPLE 44

3-Benzyl-2,4-imidazolidinedione

Hydantoin (2,4-imidazolidinedione; 25 g, 0.25 mole) was dissolved in 1 liter of 90% ethanol. Potassium hydroxide (15 g, 0.27 mole) in 125 ml of ethanol was added and the mixture stirred for 16 hours. The potassium salt was recovered by filtration and dried at 80° C. at reduced pressure [25.2 g, m.p. 271°–2° C. (dec)].

Potassium salt (5.5 g, 0.04 mole) and benzyl bromide (17.1 g, 11.9 ml, 0.10 mole) were combined with 40 ml of dimethylformamide and the mixture stirred for 16 hours at room temperature and then refluxed for 4 hours. The cooled reaction mixture was filtered and the filtrate evaporated to an oil. The oil was dissolved in chloroform. The chloroform solution was washed with water and then with saturated brine, dried over anhydrous magnesium sulfate, filtered and evaporated to solids. Trituration of the solids with ether gave the title product (3.0 g, m.p. 139°–140° C., m/e 190).

By the same method, but generating a sodium salt in situ by the use of one equivalent of sodium hydride, uracil and dihydrouracil are converted to 3-benzyl-2,3(1H,3H)-pyrimidinedione and 3-benzyl-5,6-dihydro-2,3(1H,3H)-pyrimidinedione.

EXAMPLE 45

3-Benzyl-1-(4-bromo-1-butyl)-2,4-imidazolidinedione

Benzylimidazoline of the preceding Example (1.9 g, 10 mmoles) in 5 ml of dimethylformamide was added dropwise to a slurry of sodium hydride (528 mg of 50% dispersion in oil, 11 mmoles) and the mixture then stirred for 1 hour at room temperature. The resulting solution was added dropwise to 1,4-dibromobutane (2.37 g, 11 mmole) in 10 ml of dimethylformamide. After stirring 16 hours at room temperature, the reaction mixture was poured into ice and water and extracted with ethyl acetate. The organic layer was washed with saturated brine, dried over anhydrous magnesium sulfate, filtered and evaporated to an oil. The oil was chromatographed on silica gel with chloroform as eluant. Clean product fractions were combined and evaporated to yield the title product as an oil [1.4 g, pnmr(CDCl$_3$)delta 1.6–2.0 (m, 4H), 3.2–3.6 (m, 4H), 3.8 (s, 2H), 4.6 (s, 2H), 7.2–7.5 (m, 5H)].

By the same method, preferably with a larger excess of the appropriate dihaloalkane, the following compounds are prepared:
3-benzyl-1-(3-bromo-1-propyl)-2,4-imidazolidinedione;
3-benzyl-1-(4-chloro-1-butyl)-2,4-imidazolidinedione;
3-benzyl-1-(5-bromo-1-pentyl)-2,4-imidazolidinedione; and
3-benzyl-1-(6-bromo-1-hexyl)-2,4-imidazolidinedione.

By the same method, preferably with a larger excess of 1,4-dibromobutane, the other benzyl-substituted heterocycles of the preceding Example are converted to:
3-benzyl-1-(4-bromo-1-butyl)-2,3(1H,3H)-pyrimidinedione; and
3-benzyl-1-(4-bromo-1-butyl)-5,6-dihydro-2,3(1H,3H)-pyrimidinedione.

EXAMPLE 46

(±)-8-Fluoro-5-(4-fluorophenyl)-2-[4-(3-benzyl-2,4-imidazolidinedion-1-yl)-1-butyl]-2,3,4,4a,5,9b-hexahydro-4a,9b-trans-1H-pyrido[4,3-b]indole Hydrochloride (±)-8-fluoro-5-(4-fluorophenyl)-2,3,4,4a,5,9b-hexahydro-4a,9b-trans-1H-pyrido[4,3-b]indole (573 mg, 2 mmoles), bromobutylimidazolidinedione of the preceding Example (1.3 g, 4 mmoles), potassium carbonate (1.3 g, 10 mmoles) and potassium iodide (10 mg) were combined with 4-methyl-2-pentanone (25 ml). The mixture was stirred for 4 days at room temperature and then evaporated to an oil. The oil was dissolved in chloroform, washed with saturated brine, dried over anhydrous magnesium sulfate, filtered and reevaporated to a second oil. The second oil was chromatographed on 150 ml silica gel. A less polar byproduct was removed by elution with chloroform. Product was then eluted from the column with 99:1 chloroform:methanol. Clean product fractions were combined and evaporated to yield the free base form (880 mg). The free base was dissolved in ether and precipitated as a hygroscopic hydrochloride salt (560 mg) by the addition of ethereal hydrogen chloride. Recrystallization from ethyl acetate and then from chloroform/ethyl acetate gave the title product in non-hygroscopic form [250 mg, m.p. 191°–194° C. (dec)].

Analysis: Calcd. for $C_{31}H_{32}N_4O_2F_2 \cdot HCl$: C, 65.66; H, 5.86; N, 9.88. Found: C, 65.34; H, 5.73; N, 10.09.

The corresponding chloro compound is substituted for the bromo compound to yield the same product.

By the same method, the other haloalkylheterocyclic compounds of the preceding Example are converted to:

($\pm$)-8-fluoro-5-(4-fluorophenyl)-2-[3-(3-benzyl-2,4-imidazolidinedione-1-yl)-1-propyl]-2,3,4,4a,5,9b-hexahydro-4a,9b-trans-1H-pyrido[4,3-b]indole;

($\pm$)-8-fluoro-5-(4-fluorophenyl)-2-[5-(3-benzyl-2,4-imidazolidinedione-1-yl)-1-pentyl]-2,3,4,4a,5,9b-hexahydro-4a,9b-trans-1H-pyrido[4,3-b]indole;

($\pm$)-8-fluoro-5-(4-flurophenyl)-2-[6-(3-benzyl-2,4-imidazolidinedione-1-yl)-1-hexyl]-2,3,4,4a,5,9b-hexahydro-4a,9b-trans-1h-pyrido[4,3-b]indole;

($\pm$)-8-fluoro-5-(4-fluorophenyl)-2-[[4-[3-benzyl-2,3(1H,3H)-pyrimidinedion-1-yl]-1-butyl]]-2,3,4,4a,5,9b-hexahydro-4a,9b-trans-1H-pyrido[4,3-b]indole; and ($\pm$)-8-fluoro-5-(4-fluorophenyl)-2-[[4-[3-benzyl-5,6-dihydro-2,3(1H,3H)-pyrimidinedion-1-yl]-1-butyl]]-2,3,4,4a,5,9b-hexahydro-4a,9b-trans-1H-pyrido[4,3-b]indole.

EXAMPLE 47

($\pm$)-8-Fluoro-5-(4-fluorophenyl)-2-[4-(2,4-imidazolidinedion-1-yl)-1-butyl]-2,3,4,4a,5,9b-hexahydro-4a,9b-trans-1H-pyrido[4,3-b]indole By the method of Example 4, the title compound of the preceding Example is debenzylated to yield the title compound of the present Example.

By the same method the other benzyl derivatives of the preceding Example are debenzylated to yield:

($\pm$)-8-fluoro-5-(4-fluorophenyl)-2-[3-(2,4-imidazolidinedion-1-yl)-1-propyl]-2,3,4,4a,5,9b-hexahydro-4a,9b-trans-1H-pyrido[4,3-b]indole;

($\pm$)-8-fluoro-5-(4-fluorophenyl)-2-[5-(2,4-imidazolidinedion-1-yl)-1-pentyl]-2,3,4,4a,5,9b-hexahydro-4a,9b-trans-1H-pyrido[4,3-b]indole;

($\pm$)-8-fluoro-5-(4-fluorophenyl)-2-[6-(2,4-imidazolidinedion-1-yl)-hexyl]-2,3,4,4a,5,9b-hexahydro-4a,9b-trans-1H-pyrido[4,3-b]indole;

($\pm$)-8-fluoro-5-(4-fluorophenyl)-2-[[4-[2,3(1H,3H)-pyrimidinedion-1-yl]-butyl]]-2,3,4,4a,5,9b-hexahydro-4a,9b-trans-1H-pyrido[4,3-b]indole; and ($\pm$)-8-fluoro-5-(4-fluorophenyl)-2-[[4-[5,6-dihydro-2,3(1H,3H)-pyrimidinedion-1-yl]-butyl]]-2,3,4,4a,5,9b-hexahydro-4a,9b-trans-1H-pyrido[4,3-b]indole.

EXAMPLE 48

1-(4-Bromo-1-butyl)-1,2,3,6-tetrahydro-3,6-pyridazinedione

By the method of Example 1, 3,6-dihydroxypyridazine is reacted with 1,4-dibromobutane to yield the title product.

By the same method phthalhydrazide, succinhydrazide, malonhydrazide and 2,4-pyrrolidindione are converted, respectively, to 2-(4-bromo-1-butyl)-1,2,3,4-tetrahydro-1,4-benzo[c]pyridazinedione, 1-(4-bromo-1-butyl)-hexahydro-3,6-pyridazinedione, 1-(4-bromo-1-butyl)-3,5-pyrazolidinedione and 1-(4-bromo-1-butyl)-2,4-pyrrolidinedione.

EXAMPLE 49

($\pm$)-8-Fluoro-5-(4-fluorophenyl)-2-[4-(1,2,3,6-tetrahydro-pyridazine-3,6-dion-1-yl)-1-butyl]-2,3,4,4a,5,9b-hexahydro-4a,9b-trans-1H-pyrido[4,3-b]indole By the method of Example 2, the bromobutyl derivative of the preceding Example is reacted with ($\pm$)-8-fluoro-5-(4-fluorophenyl)-2,3,4,4a,5,9b-hexahydro-4a,9b-trans-1H-pyrido[4,3-b]indole to yield the title product.

In like manner, the other bromobutyl derivatives of the preceding Example are converted to:

($\pm$)-8-fluoro-5-(4-fluorophenyl)-2-[4-(1,2,3,4-tetrahydro-1,4-benzo[c]pyridazinedion-2-yl)-1-butyl]-2,3,4,4a,5,9b-hexahydro-4a,9b-trans-1H-pyrido[4,3-b]indole;

($\pm$)-8-fluoro-5-(4-fluorophenyl)-2-[4-(hexahydro-3,6-pyridazindion-1-yl)-1-butyl]-2,3,4,4a,5,9b-hexahydro-4a,9b-trans-1H-pyrido[4,3-b]indole;

($\pm$)-8-fluoro-5-(4-fluorophenyl)-2-[4-(3,5-pyrazolidindion-1-yl)-1-butyl]-2,3,4,4a,5,9b-hexahydro-4a,9b-trans-1H-pyrido[4,3-b]indole; and ($\pm$)-8-fluoro-5-(4-fluorophenyl)-2-[4-(2,4-pyrrolidinedione-1-yl)-1-butyl]-2,3,4,4a,5,9b-hexahydro-4a,9b-trans-1H-pyrido-[4,3-b]indole.

EXAMPLE 50

2-(4-Chloro-1-butyl)-3(2H)-benz[d]isothiazolone 1,1-Dioxide

Sodium saccharin (5.6 g, 0.027 mole) and 1,4-dichlorobutane (14.9 ml, 0.135 mole) were taken into 100 ml of dimethylformamide and heated on a steam bath for 4 hours. The reaction mixture was evaporated in vacuo to an oil and the oil extracted with 100 ml of hexane. Residual hexane was removed from the remaining oil by vacuum evaporation to yield the title product (956 mg).

EXAMPLE 51

($\pm$)-8-Fluoro-5-(4-fluorophenyl)-2-[[4-[1,1-dioxo-3(2H)-benz[d]isothiazolon-2-yl]-1-butyl]]-2,3,4,4a,5,9b-trans-1H-pyrido[4,3-b]indole Hydrochloride The title compound of the preceding Example (956 mg, 3.5 mmoles), ($\pm$)-8-fluoro-5-(4-fluorophenyl)-2,3,4,4a,5,9b-hexahydro-4a,9b-trans-1H-pyrido[4,3-b]indole (500 mg, 1.75 mmoles), anhydrous sodium carbonate (1.1 g, 10.5 mmoles) and potassium iodide (5 mg) were reacted in 3-methyl-2-butanone (20 ml) by the method of Example 2. Following the 16 hour reflux period, the reaction mixture was evaporated to gum and the gum chromatographed on silica gel with 1:1 methylene chloride:ethyl acetate as eluant. The column was monitored by tlc; single component product fractions were combined and evaporated to a second gum. The second gum was dissolved in ether, acidified with ethereal hydrogen chloride and the resulting suspension evaporated to yield the title product [339 mg; Rf 0.45 (1:1 methylene chloride:ethyl acetate)].

Analysis: Calcd. for $C_{28}H_{27}N_3O_3SF_2 \cdot HCl \cdot H_2O$: C, 58.18; H, 5.23; N, 7.26. Found: C, 57.90; H, 5.21; N, 7.07.

EXAMPLE 52

(±)-8-Fluoro-5-(4-fluorophenyl)-2-[4-(2,3-dihydro-2,3(1H)-isoindoledione-2-yl)-1-butyl]-2,3,4,4a,5,9b-hexahydro-4a,9b-trans-1H-pyrido[4,3-b]indole Hydrochloride By the procedure of Example 2, N-(4-bromo-1-butyl)-phthalimide (0.985 g, 3.5 mmoles) was converted to the title product. The crude product isolated from the water/methylene chloride partition was chromatographed on silica gel with 1:1 ethyl acetate:methylene chloride as eluant and tlc monitoring. Clean product fractions were combined and evaporated to a gum. The gum was dissolved in ether and converted to hydrochloride salt by the addition of ethereal hydrogen chloride. The resulting suspension was taken to dryness and the residue crystallized from acetone to yield the title product [425 mg, m.p. 169°–171° C., Rf 0.55 (1:1 ethyl acetate:methylene chloride)].

Analysis: Calcd. for $C_{29}H_{27}N_3O_2F_2 \cdot HCl \cdot H_2O$: C, 64.26; H, 5.57; N, 7.75. Found: C, 64.01; H, 5.14; N, 7.64.

By the same method N-(4-bromo-1-butyl)succinimide, N-(4-bromo-1-butyl)glutarimide and N-(4-bromo-1-butyl)-maleimide are converted, respectively, to:

(±)-8-fluoro-5-(4-fluorophenyl)-2-[4-(2,5-pyrrolidinedion-1-yl)-1-butyl]-2,3,4,4a,5,9b-hexahydro-4a,9b-trans-1H-pyrido[4,3-b]indole;

(±)-8-fluoro-5-(4-fluorophenyl)-2-[4-(2,6-piperidinedione-1-yl)-1-butyl]-2,3,4,4a,5,9b-hexahydro-4a,9b-trans-1H-pyrido[4,3-b]indole; and (±)-8-fluoro-5-(4-fluorophenyl)-2-[4-(3-pyrroline-2,5-dion-1-yl)-1-butyl]-2,3,4,4a,5,9b-hexahydro-4a,9b-trans-1H-pyrido[4,3-b]indole.

EXAMPLE 53

3-(4-Chloro-1-butyl)-2,4-thiazolidinedione

By the procedure of Example 1, 2,4-thiazolidinedione (8 g, 0.068 mole) was converted to the title product. The reaction mixture was filtered and evaporated to an oil. The oil was triturated with methylene chloride, solids removed by filtration and the filtrate reevaporated to yield the desired product as an oil [Rf 0.2 (4:1 ethyl acetate:methanol)].

By the same procedure, 3,4,5,6-tetrahydro-1,3(2H)-thiazine-2,4-dione is converted to 3-(4-chloro-1-butyl)-3,4,5,6-tetrahydro-1,3(2H)-thiazine-2,4-dione.

EXAMPLE 54

(±)-8-Fluoro-5-(4-fluorophenyl)-2-[4-(2,4-thiazolidinedione-3-yl)-1-butyl]-2,3,4,4a,5,9b-hexahydro-4a,9b-trans-1H-pyrido[4,3-b]indole Hydrochloride By the procedure of Example 2, the chlorobutylthiazolidine of the preceding Example (543 mg, 2.62 mmole) was converted to the crude free base form of the title compound.

The crude base was chromatographed on silica gel with ethanol as eluant and tlc monitoring. Clean product fractions were combined and evaporated to a gum. The gum was dissolved in ether and acidified with ethereal hydrogen chloride. Evaporation to solids and reslurry in hexane gave the title product (479 mg, hygroscopic).

Analysis: Calcd. for $C_{24}H_{25}F_2O_2N_3S \cdot HCl \cdot 1.2\ H_2O$: C, 55.90; H, 5.51; N, 8.15. Found: C, 55.57; H, 4.96; N, 8.01.

By the same procedure the chlorobutylthiazine of the preceding Example is converted to:

(±)-8-fluoro-5-(4-fluorophenyl)-2-[4-(3,4,5,6-tetrahydro-1,3(2H)-thiazine-2,4-dione-3-yl)-1-butyl]-2,3,4,4a,5,9b-hexahydro-4a,9b-trans-1H-pyrido[4,3-b]indole.

EXAMPLE 55

(±)-8-Fluoro-5-(4-fluorophenyl)-2-[2-(2,4-imidazolidinedion-3-yl)ethyl]-2,3,4,4a,5,9b-hexahydro-4a,9b-trans-1H-pyrido[4,3-b]indole By the procedure of Example 2, (±)-8-fluoro-5-(4-fluorophenyl)-2,3,4,4a,5,9b-hexahydro-4a,9b-trans-1H-pyrido[4,3-b]indole (573 mg, 2 mmoles) was reacted with 3-(2-bromoethyl)-2,4-imidazolidinedione (828 mg, 4 mmoles) to form the title product. The reaction mixture was filtered with chloroform wash, and the combined filtrate and washings evaporated to dryness. The solid residue was chromatographed on 100 ml of silica gel with ethyl acetate as eluant and tlc monitoring. Clean product fractions were combined, evaporated to dryness, and the residue recrystallized from chloroform/hexane to yield the title product [444 mg, m.p. 195°–197° C. (dec)]. For analysis, 200 mg was further recrystallized from methanol [180 mg, m.p. 191°–193° C. (dec)].

Analysis: Calcd. for $C_{22}H_{22}F_2N_4O_2$: C, 64.07; H, 5.38; N, 13.58. Found: C, 63.72; H, 5.47; N, 13.45.

EXAMPLE 56

3-(3-Bromo-1-propyl)-2,4-imidazolidindione

The potassium salt of 2,4-imidazolinedione (hydantoin; 5.5 g, 0.04 mole; prepared as in Example 44) was reacted with 1,3-dibromopropane (14.3 ml, 0.14 mole) in 50 ml of dimethylformamide for 16 hours at room temperature and then for 2 hours at reflux. The reaction mixture was filtered, evaporated to dryness, and the residue recrystallized from isopropyl alcohol (950 mg, m.p. 103°–106° C., m/e 222/220).

EXAMPLE 57

(±)-8-Fluoro-5-(4-fluorophenyl)-2-[3-(2,4-imidazolidinedion-3-yl)-1-propyl]-2,3,4,4a,5,9b-hexahydro-4a,9b-trans-1H-pyrido[4,3-b]indole Methanesulfonate (±)-8-fluoro-5-(4-fluorophenyl)-2,3,4,4a,5,9b-hexahydro-4a,9b-trans-1H-pyrido[4,3-b]indole (573 mg, 2 mmoles) and 3-(3-bromo-1-propyl)-2,4-imidazolidindione (884 mg, 4 mmoles), sodium carbonate (1.06 g, 10 mmoles), potassium iodide (10 mg) and 10 ml of 4-methyl-2-pentanone were combined and the mixture heated at 80°–90° C. for 5 hours. At this time tlc monitoring (9:1 chloroform:methanol) indicated complete consumption of the pyridoindole starting material. The reaction mixture was filtered and the filtrate evaporated to dryness. The residue was dissolved in ethanol and ether added to the cloud point, allowed to stand for 16 hours, filtered and the filtrate evaporated to dryness to yield the free base form of the title product (900 mg). Free base was dissolved in ethanol. Two equivalents of methanesulfonic acid were added. The title product (mesylate salt) crystallized on standing and was recovered by filtration [530 mg, m.p. 246°–249° C. (dec); m/e 426].

Analysis: Calcd. for $C_{23}H_{24}N_4O_2F_2 \cdot CH_4SO_3 \cdot 0.33\ H_2O$: C, 54.54; H, 5.47; N, 10.60. Found: C, 54.48; H, 5.33; N, 10.66.

EXAMPLE 58

3-(6-Bromo-1-hexyl)-2,4-imidazolidinedione

By the procedure of Example 56, 1,6-dibromohexane (24.2 g, 0.10 mole) was reacted to form title product. The reaction mixture was filtered, the filtrate evaporated to an oil and the oil dissolved in chloroform. The chloroform solution was washed with water and then saturated brine, dried over anhydrous magnesium sulfate, filtered and evaporated to a second oil, which crystallized from ether/hexane (3.7 g, m.p. 84°–86° C., m/e 264/262).

By the same procedure 2,4-dihydroxypyrimidine[2,4(1H,3H)-pyrimidinedione] and 5,6-dihydrouracil (hexahydro-2,4-pyrimidinedione) are converted to 3-(6-bromo-1-hexyl)-2,4(1H,3H)pyrimidinedione and 3-(6-bromo-1-hexyl)hexahydro-2,4-pyrimidinedione.

EXAMPLE 59

(±)-8-Fluoro-5-(4-fluorophenyl)-2-[6-(2,4-imidazolidinedion-3-yl)-1-hexyl]-2,3,4,4a,5,9b-hexahydro-1H-pyrido[4,3-b]indole Hydrochloride By the procedure of Example 55, 3-(6-bromo-1-hexyl)-2,4-imidazolidinedione (1.05 g, 0.04 moles) was reacted to form the title product, except that the eluant on chromatography was 19:1 chloroform-methanol. The free base was isolated as an oil from the clean column fractions. The base was dissolved in ethanol and ethanolic hydrogen chloride added to precipitate the hydrochloride. Two recrystallizations from ethanol gave the title product in purified form (220 mg, m.p. 168°–171° C.).

Analysis: Calcd. for $C_{26}H_{30}F_2N_4O_2 \cdot HCl \cdot 0.5 H_2O$: C, 60.75; H, 6.28; N, 10.90. Found: C, 60.47; H, 5.90; N, 10.82.

By the same method, the other 6-bromohexyl derivatives of the preceding Example are converted to:
(±)-8-fluoro-5-(4-fluorophenyl)-2-[6-(2,4(1H,3H)-pyrimidindion-3-yl)-1-hexyl]-2,3,4,4a,5,9b-hexahydro-4a,9b-trans-1H-pyrido[4,3-b]indole; and
(±)-8-fluoro-5-(4-fluorophenyl)-2-[6-(hexahydro-2,4-pyrimidinedion-3-yl)-1-hexyl]-2,3,4,4a,5,9b-hexahydro-4a,9b-trans-1H-pyrido[4,3-b]indole.

EXAMPLE 60

8-Fluoro-5-(4-fluorophenyl)-2-[4-(2-piperidon-1-yl)-1-butyl]-2,3,4,5-tetrahydro-1H-pyrido[4,3-b]indole Hydrochloride By the method of Example 2, 8-fluoro-5-(4-fluorophenyl)-2,3,4,5-tetrahydro-1H-pyrido[4,3-b]indole (2 g, 7.0 mmoles) was reacted with 1-(4-chloro-1-butyl)-2-piperidone (1.98 g, 10.5 mmoles) to yield crude free base, a gum. The crude base was chromatographed on silica gel, with ethyl acetate as eluant. Clean product fractions were evaporated to dryness, taken up in acetone and the title product precipitated by the addition of ethereal hydrogen chloride (1.2 g, m.p. 202°–205° C.).

Analysis: Calcd. for $C_{26}H_{29}F_2N_3O \cdot HCl \cdot 0.5 H_2O$: C, 64.65; H, 6.21; N, 8.70. Found: C, 64.75; H, 6.37; N, 8.58.

By the same method the other haloalkylpiperidones of Examples 1 and 6 are converted to:
8-fluoro-5-(4-fluorophenyl)-2-[2-(2-piperidon-1-yl)-ethyl]-2,3,4,5-tetrahydro-1H-pyrido[4,3-b]indole;
8-fluoro-5-(4-fluorophenyl)-2-[3-(2-piperidon-1-yl)-1-propyl]-2,3,4,5-tetrahydro-1H-pyrido[4,3-b]indole;
8-fluoro-5-(4-fluorophenyl)-2-[5-(2-piperidon-1-yl)-1-pentyl]-2,3,4,5-tetrahydro-1H-pyrido[4,3-b]indole;
8-fluoro-5-(4-fluorophenyl)-2-[6-(2-piperidon-1-yl)-1-hexyl]-2,3,4,5-tetrahydro-1H-pyrido[4,3-b]indole;
8-fluoro-5-(4-fluorophenyl)-2-[7-(2-piperidon-1-yl)-1-heptyl]-2,3,4,5-tetrahydro-1H-pyrido[4,3-b]indole;
8-fluoro-5-(4-fluorophenyl)-2-[8-(2-piperidon-1-yl)-1-octyl]-2,3,4,5-tetrahydro-1H-pyrido[4,3-b]indole; and
8-fluoro-5-(4-fluorophenyl)-2-[9-(2-piperidon-1-yl)-1-nonyl]-2,3,4,5-tetrahydro-1H-pyrido[4,3-b]indole.

By the same method, substituting 1-(4-chloro-1-butyl)-2-piperidone with 1-(4-chloro-1-butyl)-2-pyrrolidinone, N-(4-chloro-1-butyl)-6-hexanelactam, the following compounds are prepared:
8-fluoro-5-(4-fluorophenyl)-2-[4-(2-pyrrolidinon-1-yl)-1-butyl]-2,3,4,5-tetrahydro-1H-pyrido[4,3-b]indole; and
8-fluoro-5-(4-fluorophenyl)-2-[4-(2-perhydroazepinon-1-yl)-1-butyl]-2,3,4,5-tetrahydro-1H-pyrido[4,3-b]indole.

By the same method the appropriately substituted 5-phenyl-2,3,4,5-tetrahydro-1H-pyrido(4,3-b]indoles are converted to:
5-phenyl-2-[4-(2-piperidon-1-yl)-1-butyl]-2,3,4,5-tetrahydro-1H-pyrido[4,3-b]indole;
8-fluoro-5-(2-fluorophenyl)-2-[4-(2-piperidon-1-yl)-1-butyl]-2,3,4,5-tetrahydro-1H-pyrido[4,3-b]indole;
8-fluoro-5-(3-chlorophenyl)-2-[4-(2-piperidon-1-yl)-1-butyl]-2,3,4,5-tetrahydro-1H-pyrido[4,3-b]indole;
8-fluoro-5-(4-ethylphenyl)-2-[4-(2-piperidon-1-yl)-1-butyl]-2,3,4,5-tetrahydro-1H-pyrido[4,3-b]indole;
8-fluoro-5-(4-fluoro-2-methyl)-2-[4-(2-piperidon-1-yl)-1-butyl]-2,3,4,5-tetrahydro-1H-pyrido[4,3-b]indole;
8-chloro-5-(4-chlorophenyl)-2-[4-(2-piperidon-1-yl)-1-butyl]-2,3,4,5-tetrahydro-1H-pyrido[4,3-b]indole;
8-ethyl-5-(4-ethylphenyl)-2-[4-(2-piperidon-1-yl)-1-butyl]-2,3,4,5-tetrahydro-1H-pyrido[4,3-b]indole; and
8-methoxy-5-(4-methoxyphenyl)-2-[4-(2-piperidon-1-yl)-1-butyl]-2,3,4,5-tetrahydro-1H-pyrido[4,3-b]indole.

EXAMPLE 61

8-Fluoro-5-(4-fluorophenyl)-2-(5-cyano-1-pentyl)-2,3,4,5-tetrahydro-1H-pyrido[4,3-b]indole 8-fluoro-5-(4-fluorophenyl)-2,3,4,5-tetrahydro-1H-pyrido[4,3-b]indole (10.8 g, 0.034 mole), 6-bromohexanenitrile (6.5 g, 0.037 mole), anhydrous sodium carbonate (21.6 g, 0.204 mole), potassium iodide (100 mg) and 3-methyl-2-butanone (250 ml) were combined and the mixture refluxed for 24 hours. The reaction mixture was cooled, diluted with 250 ml of water and stirred to dissolve excess sodium carbonate. The layers were separated and the aqueous layer extracted with 200 ml of methylene chloride. The organic layers were combined, dried over anhydrous magnesium sulfate, filtered and evaporated to an oil. Addition of hexane gave the title product in crystalline form [11.3 g, m.p. 90°–98° C., Rf 0.5 (9:1 ethyl acetate:methanol)].

By the same method, 2-bromoethanenitrile, 3-bromopropanenitrile, 4-bromobutanenitrile, 5-bromopentanenitrile, 7-bromoheptanenitrile and 8-bromooctanenitrile are converted, respectively, to:
8-fluoro-5-(4-fluorophenyl)-2-cyanomethyl-2,3,4,5-tetrahydro-1H-pyrido[4,3-b]indole;
8-fluoro-5-(4-fluorophenyl)-2-(2-cyano-1-ethyl)-2,3,4,5-tetrahydro-1H-pyrido[4,3-b]indole;

8-fluoro-5-(4-fluorophenyl)-2-(3-cyano-1-propyl)-
2,3,4,5-tetrahydro-1H-pyrido[4,3-b]indole;
8-fluoro-5-(4-fluorophenyl)-2-(4-cyano-1-butyl)-2,3,4,5-
tetrahydro-1H-pyrido[4,3-b]indole;
8-fluoro-5-(4-fluorophenyl)-2-(6-cyano-1-hexyl)-2,3,4,5-
tetrahydro-1H-pyrido[4,3-b]indole; and
8-fluoro-5-(4-fluorophenyl)-2-(7-cyano-1-heptyl)-
2,3,4,5-tetrahydro-1H-pyrido[4,3-b]indole.

EXAMPLE 62

8-Fluoro-5-(4-fluorophenyl)-2-(6-amino-1-hexyl)-
2,3,4,5-tetrahydro-1H-pyrido[4,3-b]indole At room temperature, the title compound of the preceding Example (11.3 g, 0.03 moles) was stirred in 500 ml of ether for 15 minutes, by which time almost complete solution has resulted. Lithium aluminum hydride (3.0 g) was added in portions with vigorous stirring. After stirring for an additional 1.5 hours, about 5 g of Glauber's salt was added in five 1 g portions and stirring continued for 15 minutes. Solids were removed by filtration with tetrahydrofuran wash. The combined filtrate and wash was evaporated to yield the title product as an oil [10.7 g; Rf 0.1 (9:1 ethyl acetate:methanol), 0.1 (9:1 methanol:acetate acid)].

By the same method, the other nitriles of the preceding Example are converted to:
8-fluoro-5-(4-fluorophenyl)-2-aminoethyl)-2,3,4,5-tetrahydro-1H-pyrido[4,3-b]indole;
8-fluoro-5-(4-fluorophenyl)-2-(3-amino-1-propyl)-
2,3,4,5-tetrahydro-1H-pyrido[4,3-b]indole;
8-fluoro-5-(4-fluorophenyl)-2-(4-amino-1-butyl)-2,3,4,5-
tetrahydro-1H-pyrido[4,3-b]indole;
8-fluoro-5-(4-fluorophenyl)-2-(5-amino-1-pentyl)-
2,3,4,5-tetrahydro-1H-pyrido[4,3-b]indole;
8-fluoro-5-(4-fluorophenyl)-2-(7-amino-1-heptyl)-
2,3,4,5-tetrahydro-1H-pyrido[4,3-b]indole; and
8-fluoro-5-(4-fluorophenyl)-2-(8-amino-1-octyl)-2,3,4,5-
tetrahydro-1H-pyrido[4,3-b]indole.

EXAMPLE 63

8-Fluoro-5-(4-fluorophenyl)-2-(6-acetamido-1-hexyl)-
2,3,4,5-tetrahydro-1H-pyrido[4,3-b]indole At room temperature, the title amino compound of the preceding Example (10.7 g, 0.028 mole) was dissolved in 80 ml of methylene chloride. Triethylamine (15.6 ml, 0.112 mole) was added and then, in a dropwise manner, acetyl chloride (2.35 g, 0.030 mole) in 20 ml of methylene chloride. A mild exotherm was noted. The mixture was stirred for 30 minutes more, then concentrated to an oil (14 g). The oil was chromatographed on silica gel with 1:1 methanol:ethyl acetate as eluant and tlc monitoring. Clean product fractions were combined, evaporated to dryness and the residue crystallized from ether to yield the title product in purified form [6.33 g; m.p. 114°–116° C.; Rf 0.6 (1:1 methanol:ethyl acetate)].

Analysis: Calcd. for $C_{25}H_{29}ON_3F_2$: C, 70.56; H, 6.87; N, 9.88. Found: C, 70.34; H, 6.96; N, 9.66.

By the same method, the other amino compounds of the preceding Example are converted to:
8-fluoro-5-(4-fluorophenyl)-2-(2-acetamidoethyl)-
2,3,4,5-tetrahydro-1H-pyrido[4,3-b]indole;
8-fluoro-5-(4-fluorophenyl)-2-(3-acetamido-1-propyl)-
2,3,4,5-tetrahydro-1H-pyrido[4,3-b]indole;
8-fluoro-5-(4-fluorophenyl)-2-(4-acetamido-1-butyl)-
2,3,4,5-tetrahydro-1H-pyrido[4,3-b]indole;
8-fluoro-5-(4-fluorophenyl)-2-(5-acetamido-1-pentyl)-
2,3,4,5-tetrahydro-1H-pyrido[4,3-b]indole;
8-fluoro-5-(4-fluorophenyl)-2-(7-acetamido-1-heptyl)-
2,3,4,5-tetrahydro-1H-pyrido[4,3-b]indole; and
8-fluoro-5-(4-fluorophenyl)-2-(8-acetamido-1-octyl)-
2,3,4,5-tetrahydro-1H-pyrido[4,3-b]indole.

By the same method, substituting the appropriate anhydride or acid chloride for acetyl chloride [specifically acetoformic acid reagent, cf. Blackwood et al., J. Am. Chem. Soc. 82, pp. 5194–5197 (1960), in the case of the formyl derivative], the following compounds are prepared:
8-fluoro-5-(4-fluorophenyl)-2-(6-formamido-1-hexyl)-
2,3,4,5-tetrahydro-1H-pyrido[4,3-b]indole;
8-fluoro-5-(4-fluorophenyl)-2-(6-isobutyrylamino-1-hexyl)-2,3,4,5-tetrahydro-1H-pyrido[4,3-b]indole;
8-fluoro-5-(4-fluorophenyl)-2-(6-isovalerylamino-1-hexyl)-2,3,4,5-tetrahydro-1H-pyrido[4,3-b]indole; and
8-fluoro-5-(4-fluorophenyl)-2-(6-heptanoylamino-1-hexyl)-2,3,4,5-tetrahydro-1H-pyrido[4,3-b]indole.

EXAMPLE 64

8-Fluoro-5-(4-fluorophenyl)-2-(6-ethoxycarbonylamino-1-hexyl)-2,3,4,5-tetrahydro-1H-pyrido[4,3-b]indole Following the procedure of the preceding Example, 8-fluoro-5-(4-fluorophenyl)-2-(6-amino-1-hexyl)-2,3,4,5-tetrahydro-1H-pyrido[4,3-b]indole (1.6 g, 4.2 mmoles) was reacted with ethylchloroformate (0.45 ml, 4.6 moles) in methylene chloride (5 ml) in the presence of triethylamine (2.3 ml, 16.7 mmoles), and the title product isolated and purified, except that ethyl acetate was used as eluant in the silica gel chromatography (365 mg, m.p. 159°–162° C.).

Analysis: Calcd. for $C_{26}H_{31}O_2N_3F_2 \cdot HCl \cdot 0.75\ H_2O$: C, 61.77; H, 6.33; N, 8.31. Found: C, 61.84; H, 6.47; N, 8.33.

By the same method, substituting the appropriate alkyl chloroformate for ethyl chloroformate, the following compounds are prepared:
8-fluoro-5-(4-fluorophenyl)-2-(6-methoxycarbonylamino-1-hexyl)-2,3,4,5-tetrahydro-1H-pyrido[4,3-b]indole;
8-fluoro-5-(4-fluorophenyl)-2-(6-isopropoxycarbonylamino-1-hexyl)-2,3,4,5-tetrahydro-1H-pyrido[4,3-b]indole; and
8-fluoro-5-(4-fluorophenyl)-2-(1-hexyloxycarbonylamino-1-hexyl)-2,3,4,5-tetrahydro-1H-pyrido[4,3-b]indole.

We claim:

1. A (+) enantiomeric, a mixture of (+) and (−) enantiomeric or (±) racemic 4a,9b-trans-hexahydro-1H-pyridoindole derivative of the formula

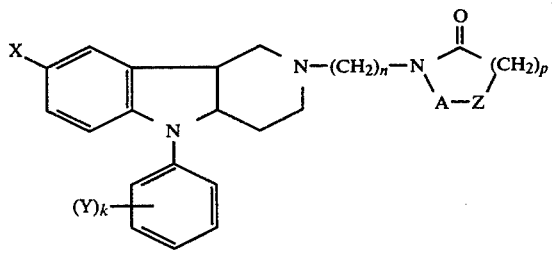

or a pharmaceutically acceptable salt thereof, wherein
k is 1 or 2;
n is 2 to 9;
p is 0 or 1;

X and Y are each independently H, F, Cl, Br, $OCH_3$, $CH_3$ or $CH_2CH_3$;

A is methano, ethano, propano, etheno, o-benzeno, or a mono or disubstituted form of o-benzeno, the monosubstituent and each of the disubstituents being independently F, Cl, Br, $OCH_3$, $CH_3$ or $CH_2CH_3$ with the proviso that when A is methano, p is 1;

Z is methano, oxygen, sulfur or $NR^2$; and $R^2$ is H, $(C_1-C_5)$alkyl, phenyl, benzyl or a ring mono or disubstituted form of phenyl or benzyl, the monosubstituent and each of the disubstituents being independently F, Cl, Br, $OCH_3$, $CH_3$ or $CH_2CH_3$.

2. A derivative of claim 1 wherein k is 1, X is F and Y is para F.

3. A derivative of claim 2 wherein A is ethano and n is 3 to 6.

4. A derivative of claim 3 wherein p is 1 and Z is methylene.

5. The (+) enantiomeric or racemic derivative of claim 4 wherein n is 4.

6. The (+) enantiomeric or racemic derivative of claim 4 wherein n is 5.

7. The (+) enantiomeric or racemic derivative of claim 4 wherein n is 6.

8. A derivative of claim 3 wherein p is 0 and Z is oxygen.

9. The (+) enantiomeric or racemic derivative of claim 8 wherein n is 4.

10. The (+) enantiomeric or racemic derivative of claim 8 wherein n is 5.

11. The (+) enantiomeric or racemic derivative of claim 8 wherein n is 6.

12. A method of treating psychoses and neuroses in a patient requiring major tranquilization which comprises administering to the patient by oral, intravenous, intramuscular or subcutaneous route an effective amount of a compound of claim 1.

* * * * *